US008379206B2

(12) United States Patent
Kachanov et al.

(10) Patent No.: US 8,379,206 B2
(45) Date of Patent: Feb. 19, 2013

(54) METHOD AND APPARATUS FOR THE PHOTO-ACOUSTIC IDENTIFICATION AND QUANTIFICATION OF ANALYTE SPECIES IN A GASEOUS OR LIQUID MEDIUM

(75) Inventors: Alexander Kachanov, San Jose, CA (US); Serguei Koulikov, Mountain View, CA (US)

(73) Assignee: LI-COR, Inc., Lincoln, NE (US)

( * ) Notice: Subject to any disclaimer, the term of this patent is extended or adjusted under 35 U.S.C. 154(b) by 12 days.

(21) Appl. No.: 13/105,779

(22) Filed: May 11, 2011

(65) Prior Publication Data

US 2011/0214480 A1    Sep. 8, 2011

Related U.S. Application Data

(63) Continuation of application No. 12/660,614, filed on Mar. 2, 2010.

(51) Int. Cl.
  *G01N 21/00*  (2006.01)
(52) U.S. Cl. ....................................... 356/436
(58) Field of Classification Search ............ 356/436
  See application file for complete search history.

(56) References Cited

U.S. PATENT DOCUMENTS

| | | |
|---|---|---|
| 3,938,365 A | 2/1976 | Dewey |
| 5,528,040 A | 6/1996 | Lehmann et al. |
| 5,912,740 A | 6/1999 | Zare et al. |
| 5,929,981 A | 7/1999 | Keilbach |
| 5,973,864 A | 10/1999 | Lehmann et al. |
| 6,466,322 B1 | 10/2002 | Paldus et al. |
| 6,504,145 B1 | 1/2003 | Romanini et al. |
| 6,608,683 B1 | 8/2003 | Pilgrim et al. |
| 6,618,148 B1 | 9/2003 | Pilgrim et al. |
| 7,012,696 B2 | 3/2006 | Orr et al. |
| 7,069,769 B2 | 7/2006 | Kung |
| 7,245,380 B2 | 7/2007 | Kosterev |
| 7,263,871 B2 | 9/2007 | Selker et al. |
| 7,398,672 B2 | 7/2008 | Riddle |
| 7,450,240 B2 | 11/2008 | Morville et al. |
| 7,535,573 B2 | 5/2009 | Kachanov et al. |
| 7,663,756 B2 | 2/2010 | Cole |
| 7,679,750 B2 | 3/2010 | Li et al. |
| 7,765,871 B2 | 8/2010 | Riddle |

(Continued)

FOREIGN PATENT DOCUMENTS

| | | |
|---|---|---|
| JP | 07-270308 A | 10/1995 |
| WO | WO 2007/004168 A1 | 1/2007 |

(Continued)

OTHER PUBLICATIONS

Burggraf et al., "Quantitative Photoacoustic Spectroscopy of Intensely Light-Scattering Thermally Thick Samples," Anal. Chem., 1981, vol. 53, pp. 759-764.

(Continued)

*Primary Examiner* — Tara S Pajoohi Gomez
(74) *Attorney, Agent, or Firm* — Leydig, Voit & Mayer, LLP; Gerald T. Gray

(57) ABSTRACT

A method and apparatus for the photo-acoustic identification and quantification of one or more analyte species present in a gaseous or liquid medium in low concentration utilizing a laser and a resonant optical cavity containing the medium and having within the cavity at least two partially transparent mirrors, one of which is a cavity coupling mirror and one of which is moveably mounted on an assembly responsive to an input signal.

18 Claims, 15 Drawing Sheets

U.S. PATENT DOCUMENTS

| | | |
|---|---|---|
| 7,805,980 B2 | 10/2010 | Kosterev |
| 2004/0065816 A1 | 4/2004 | Ye et al. |
| 2006/0084180 A1 | 4/2006 | Paldus et al. |
| 2006/0119851 A1 | 6/2006 | Bounaix |
| 2006/0123884 A1 | 6/2006 | Selker et al. |
| 2008/0134756 A1 | 6/2008 | Riddle |
| 2008/0151248 A1 | 6/2008 | Cole et al. |
| 2008/0196477 A1* | 8/2008 | Van Herpen et al. ......... 73/24.02 |
| 2009/0229345 A1 | 9/2009 | Van Kesteren |
| 2009/0249861 A1 | 10/2009 | Van Dijk et al. |
| 2010/0002234 A1 | 1/2010 | Cormier et al. |
| 2010/0011836 A1 | 1/2010 | Kalkman et al. |

FOREIGN PATENT DOCUMENTS

| | | | |
|---|---|---|---|
| WO | WO2008/026189 | * | 3/2008 |

OTHER PUBLICATIONS

Hippler et al., "Cavity-enhanced resonant photoacoustic spectroscopy with optical feedback cw diode lasers: A novel technique for ultratrace gas analysis and high-resolution spectroscopy," The Journal of Chemical Physics, 2010, vol. 133, pp. 044308-1-044308-8.

Clairon, A. et al., "Frequency Noise Analysis of Optically Self-Locked Diode Lasers," IEEE J. Quantum Electronics, 25(6):1131-1142 (1989).

International Search Report and Written Opinion for PCT/US2011/049453 dated Mar. 23, 2012.

International Search Report and Written Opinion for PCT/US2011/026922 dated Apr. 27, 2011.

Kosterev, A. A. et al., "Quartz-enhanced photoacoustic spectroscopy," Optics Letters 27(21):1902-1904 (Nov. 1, 2002).

Kosterev, A. A. et al., "Trace Humidity Sensor based on Quartz-Enhanced Photoacoustic Spectroscopy," LACSEA 2006, Incline Village, NV, Feb. 5-9, 2006.

Non-Final Office Action issued Jun. 22, 2012 in U.S. Appl. No. 13/105,786.

Rossi, A. et al., "Optical enhancement of diode laser-photoacoustic trace gas detection by means of external Fabry-Perot cavity," Appl. Phys. Lett. 87, 041110 (2005).

* cited by examiner

METHOD AND APPARATUS FOR THE PHOTO-ACOUSTIC IDENTIFICATION AND QUANTIFICATION OF ANALYTE SPECIES IN A GASEOUS OR LIQUID MEDIUM

CROSS-REFERENCES TO RELATED APPLICATIONS

The present application is a continuation of U.S. patent application Ser. No. 12/660,614, filed Mar. 2, 2010, which is hereby incorporated by reference in its entirety for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This invention belongs to the field of ultra-sensitive analysis of gaseous species or more specifically, to spectroscopic methods of analysis such as, for example, Photo Acoustic Spectroscopy (PAS) that benefit from a high intensity light source. PAS has been among the methods of ultra-sensitive spectroscopy popular in scientific research, but to date it has had a very limited impact on the gas sensing industry. Many years of PAS research as an analytical method has resulted in a general understanding of the nature of the photo acoustic effect and of a suitable configuration for photo acoustic cells. Classical PAS (a microphone and a resonant acoustic cell) have reached a high level of operating performance. As evidence of such is the fact that the best results demonstrated in recent years by different groups e.g., [A. Miklos, et. al., Rev. Sci. Intr., 72(4), 1937-1955 (2001); M. Webber, et. al., Appl. Opt., 42(12), 2119-2126 (2003) and V. Kapitanov, et. al., Appl. Phys. B, 90, 235-241 (2008)] are very close and report values for normalized noise equivalent absorption (NNEA) of from 1.5 to $2.5 \times 10^{-9}$ cm$^{-1}$ W/Hz$^{1/2}$. This means that with such a photo-acoustic cell an absorption coefficient k between $1.5 \times 10^{-9}$ cm$^{-1}$ and $2.5 \times 10^{-9}$ cm$^{-1}$ can be detected with a signal to noise ratio of one using a laser source power of 1 W, provided that the equivalent noise bandwidth of the detection electronics is equal to 1 Hz. However, the sensitive general purpose microphones used in PAS required elaborate acoustic isolation of the sample cells, and low immunity to ambient noise may be a reason impeding its use in noisy industrial environments. Less than a decade ago a quartz tuning fork (QTF) was introduced as a novel photo acoustic sensor, see [U.S. Pat. No. 7,245,380 (2002) and A. Kosterev, et. al., Optics Letters, 27(21), 1902-1904 (2002)]. The QTF is sensitive to the local pressure variation due to the optical absorption between the fork tines, but it has a high immunity to ambient acoustic perturbations coming in the form of plane waves. The method has been named QEPAS—Quartz Enhanced Photo Acoustic Spectroscopy. QEPAS has reached the same performance level in sensitivity as conventional PAS, [see A. Kosterev, et. al., Optics Letters, 27(21), 1902-1904 (2002)], but with the important advantage of a very small sensor size. Surprisingly however, even in 2009, seven years after the invention of QEPAS, one cannot find a single commercial gas detection product based upon QEPAS.

Yet even more surprising, there are only a few examples of commercial gas sensors based upon "classical" PAS cells despite the fact that PAS using lasers was introduced as early as in 1968 by Kerr and Atwood, see Applied Optics, 7(5), 915-922 (1968). The explanation is simple—the power of the commercially available laser sources is too low, and therefore the limits of detection on concentration are non-competitive with other methods. Only distributed feedback (DFB) lasers intended for use in the telecommunication industry, which operate in the spectral range from 1260 to 1675 nm (O to U-band), can currently meet the requirements for an industrial gas sensor, i.e., robustness, ease of use, reliability and an affordable price. The wavelength ranges for Telecommunications Optical Bands are as follows:

| Band Name | Wave length in Nanometers (nm) |
|---|---|
| O-band Original | 1260-1360 |
| E-band Extended | 1360-1460 |
| S-band Short | 1460-1530 |
| C-band Conventional | 1530-1565 |
| L-band Long | 1565-1625 |
| U-band Ultra-long | 1625-1675 |

Beyond this range, extended versions of such lasers are available from a limited number of vendors for wavelengths of up to 2350 rim, but at a significantly higher price. The output power of all such lasers is in the range of 10 to 100 mW which results in a noise equivalent absorption (NEA) of $2 \times 10^{-8}$ to $2 \times 10^{-7}$ cm$^{-1}$/Hz$^{1/2}$, both for conventional PAS and also for QEPAS. This corresponds to a noise equivalent concentration (NEC) for many important species of not higher than 0.1 ppmv/Hz$^{1/2}$, which leaves PAS using telecom DFB lasers entirely out of competition in performance with other ultra-sensitive spectroscopic techniques such as Cavity-Ring-Down Spectroscopy (CRDS) that have a NEA of about $3 \times 10^{-11}$ cm$^{-1}$/Hz$^{1/2}$. PAS has several important advantages compared to other gas detection methods, which would make it a method of choice provided that the penalty in sensitivity could be overcome. Some of these advantages have become especially attractive with the advent of Quantum Cascade Lasers (QCL) operating in the mid-IR. These advantages include:

- PAS is an intrinsically zero baseline technique, no absorption—no signal
- High immunity to interference fringes which should permit long time averaging—a big advantage relative to CRDS and ICOS
- Inexpensive microphones as detectors, as opposed to cryogenically cooled MCT photo-diodes. No need for low-noise high sensitivity, high linearity and large bandwidth detectors. All intensity monitoring can be done with low-cost detectors, a big advantage in the mid-infrared spectral range.
- The smallest detection volume with QEPAS (~1 cm$^3$ or less) permitting high-speed gas monitoring. For comparison, in CRDS the volume can be ~20 cm$^3$ and in ICOS it is about 1 liter.
- Absence of critical (and costly) optical components in contrast to CRDS and ICOS which require ultra-high reflectivity mirrors.

It is an object of the current invention to increase the sensitivity of PAS in general, and QEPAS in particular, several hundred times, and thus to bring the PAS performance (NEA) up to the level of other ultrasensitive optical sensing techniques. There are three contributing parts to the NEA of a photo-acoustic gas detector—sensor responsivity R, sensor noise N, and optical excitation power P:

$$NEA = \frac{N}{R}P. \quad (1)$$

The sensor responsivity R has units of $V/cm^{-1} \cdot W$ or $A/cm^{-1} \cdot W$ and designates the electrical signal of the acoustic signal transducer (microphone or tuning fork) per unit of optical absorption coefficient and per unit optical power. The responsivity can be increased 10 to 50 times by arranging an acoustic resonator around the acoustic signal transducer, this has been done both in PAS, [see A. Miklos, et. al., Rev. Sci. Instr., 72(4), 1937-1955 (2001); M. Webber, et. al., Appl. Opt., 42(12), 2119-2126 (2003) and V. Kapitanov, et. al., Appl. Phys. B, 90, 235-241 (2008) and in A. Kosterev, et. al., Optics Letters, 27(21), 1902-1904 (2002) and A. Kosterev et. al, LACSEA 2006, Incline Village, Nev., February 5-9 (2006)]. One can say that these acoustic resonance enhancement techniques have been generally optimized and that one cannot reasonably expect a further responsivity increase of no greater than several tens of percents. Equation (1) shows that it is not the responsivity R alone, but its ratio to the r.m.s. noise in the unit frequency bandwidth N that determines the NEA. The fundamental reason for the noise of an ideal acoustic transducer in a quiet environment should be random variations of the sound pressure in the vicinity of the sensing element due to the thermal agitation of the surrounding gas molecules. In an ideal sensor the contribution of other noise sources such as the sensor mechanical noise is due to the thermal agitation of the molecules of the sensing element itself, or otherwise the sensor pre-amplifier noise should be negligible. This is the case indeed both for sensitive compact microphones used in PAS and for QTF's used in QEPAS. This means that the detection threshold of both sensors cannot be further improved, and the only way to lower the NEA is to increase the excitation power. With semiconductor lasers operating in the C- or L-band telecommunication range the power can be increased to watts level by using an Erbium-doped fiber amplifier, [see M. Webber, et. al., Appl. Opt., 42 (12), 2119-2126 (2003)] but this solution has an unacceptably high price. Another way to increase the excitation beam power by placing the photo-acoustic cell inside the resonant cavity of a laser is obviously not applicable to DFB semiconductor lasers, and it would not be practical even with an external cavity diode laser because the power buildup is rather small in the lossy cavities of such lasers. The last remaining possibility would seem to be to increase the excitation power by intensity enhancement of the DFB laser beam in an optical power buildup cavity (OPBC). This method has been used since about 1980 in numerous laboratory atomic spectroscopy experiments. Despite these demonstrations, the first (and the only) experiment to our knowledge that used OPBC to deliver enhanced optical power to a photo-acoustic cell has been reported by Rossi and co-workers [A. Rossi, et. al., (2005), Appl. Phys. Lett., 87, 041110 (2005)]. They reported a 100 times PAS signal increase matching a 100-fold optical power buildup in the cavity with 99.0% mirrors reflectivity. However, this work cannot be considered as showing encouraging prospects for building industrial gas OPBC-PAS sensors for several reasons. First of all, the NNEA of $1.3 \times 10^{-9}$ $cm^{-1}W/\sqrt{Hz}$ that is shown by the data in [A. Rossi, et. al., (2005), Appl. Phys. Lett., 87, 041110 (2005)] was not significantly better than the value of $2 \times 10^{-9}$ $cm^{-1}W/\sqrt{Hz}$ demonstrated with "traditional" PAS, [see V. Kapitanov, et. al., Appl. Phys. B, 90, 235-241 (2008)] where a semiconductor laser was used with no OPBC enhancement. A second important reason is that the method of locking the diode laser radiation to the cavity described in the Rossi paper was only marginally effective even in a perturbation-free laboratory environment. The unstable and unreliable operation of the diode to cavity lock also resulted in very poor stability of the buildup intensity dependence as a function of time as one can see from FIG. 2 in the Rossi reference.

The most recent development in OPBC-PAS with semiconductor lasers is reported in U.S. Pat. No. 7,263,871 by Selker and co-workers. This patent teaches how a substantial power buildup of a semiconductor diode laser can be achieved using cavities of various configurations in combination with a resonant acoustic cell inside the cavity. Several methods of keeping the semiconductor laser in resonance with the optical cavity are also described in the patent, which include both electronic methods and those that take advantage of optical feedback.

The prior art discussed above describes systems for the photo-acoustic measurement of optical absorption which use passive optical cavities with a photo-acoustic sensor inside the cavity to enhance the power of the laser source by the effect of optical power buildup and to thereby increase the photo-acoustic effect.

OPBC-PAS systems currently known split into two distinct families:

i) Systems that use a chopped laser beam, which is coupled to the OPBC, such as the one described in the reference A. Rossi, et. al., (2005), Appl. Phys. Lett., 87, 041110 (2005). The optical power circulating within the cavity is modulated in amplitude. In order to maintain the laser in resonance with the cavity peak, a small frequency dither with an amplitude equal to a small fraction of the OPBC resonance peak width is applied to the laser, and the thus obtained derivative signal is used for locking. An unavoidable drawback of such approach is that the locking cannot be done during periods when the laser is off. So the cavity drives itself out of resonance during every "laser off" period. After the laser is turned on again, a large error signal results in over-reaction of the locking system, and the lock can be lost again because of this over-reaction. As a result such systems have low immunity to external perturbations, high instability of the buildup power, and are essentially useless for applications in field useable systems.

ii) Systems that constantly maintain a lock of the laser to the cavity, such as described in U.S. Pat. No. 7,263,871. The locking in such systems in very robust, especially when high-speed modulation-free locking methods are used. In such systems the circulating power is kept at a nearly constant level, and thus they can only use wavelength modulation of the laser. With the cavity being locked to the laser, the cavity mirrors oscillate, and the sound wave resulting from this oscillation is the source of a strong background signal.

The present invention features the best of both approaches by combining a very high reliability and robustness of the cavity lock to the laser, with a high efficiency photo-acoustic excitation which is not accompanied by the intense background sound.

BRIEF SUMMARY OF THE INVENTION

The present invention describes a method and apparatus for the photo-acoustic identification and quantification of one or more analyte species in a gaseous or liquid medium based upon enhancement of a low power laser radiation by locking it to an optical power buildup cavity. The method is suitably called OPBC-PAS. The invention offers a number of particular configurations of OPBC-PAS gas sensors that are especially advantageous for building compact low cost automatic sensors with high sensitivity and which are capable of long-term (e.g., years) unattended operation.

In the present invention:

the laser radiation is injected into an optical cavity the laser is modulated in wavelength and its intensity is approximately constant as a function of time the peak to peak wavelength excursion of the laser is large as compared to the cavity resonance width, which results in large intensity modulation of the power circulating inside the cavity approaching 100%. This time dependence is monitored by a first photo-detector situated behind a second cavity mirror. The strong amplitude modulation resulting from wavelength modulation of the laser is used as a source of the PAS signal. Thereby amplitude modulated PAS is performed with a wavelength modulated laser without the need to turn the laser on and off.

the phase sensitive detection at the first harmonic of the first photo-detector signal is used for constant adjustment of the cavity length, such that the carrier wavelength of the laser is always in resonance with the cavity. This cavity locking scheme does not require dithering the cavity mirror position and thus provides strong uninterrupted error signal for the cavity lock loop the PAS signal from a PAS transducer resulting from the intracavity power modulation is detected with a phase-sensitive detector at the second harmonic of the modulation frequency a second phase sensitive detector connected to the first photo-detector operating at the second harmonic and provides information about the efficiency of the PAS excitation and automatically takes into account efficiency changes that may be due to the cavity and laser ageing, the amplitude modulation of the laser intensity that may accompany the wavelength modulation, changes of the harmonic content, nonlinearity and amplitude of this unwanted amplitude modulation, and any other cause.

BRIEF DESCRIPTION OF THE DRAWINGS

The advantages of the present invention will become apparent upon reading the detailed description of the invention and the claims together with the drawings in which:

DETAILED DESCRIPTION OF THE INVENTION

We now provide a detailed description of the method of the invention and several embodiments of the apparatus applicable to the method.

Figure 1:
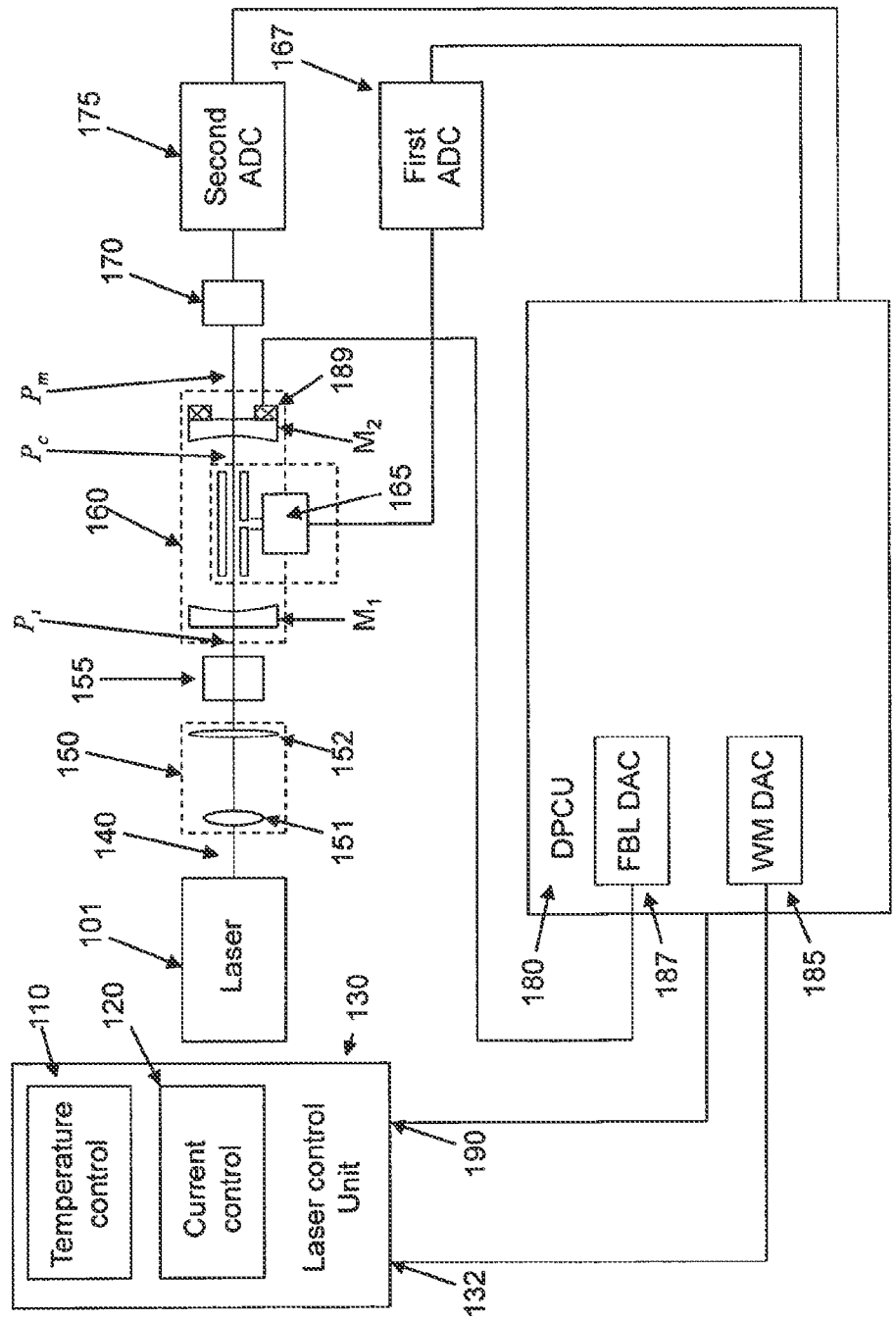
FIG. 1 is a schematic diagram representing the optical, mechanical and electronic layout of a gas detection system in accordance with the present invention.

A schematic diagram of the gas detection system of the present invention is shown in FIG. 1. The present invention in a preferred embodiment contains a semiconductor laser source 101, preferably a distributed feedback (DFB) laser emitting a single emission line that can be tuned in the vicinity of the absorption line of the analyte species of interest within a range of several wave numbers. The operating wavelength of the laser can be changed or modulated, for example, by changing the operating temperature of the semiconductor laser chip, and/or its drive current. This is accomplished by electronic modules known in the art such as a diode laser temperature controller 110 and/or a low noise diode laser current controller 120. In other embodiments the laser can be of other known type subject to the requirement that its wavelength of operation can be changed or modulated. One example of such other suitable laser type would be an external cavity semiconductor diode laser (ECDL).

The electronic and mechanical elements that are necessary to maintain the laser operation, tune its operation wavelength, apply a periodic dither waveform to the emission wavelength of the laser (otherwise called a "wavelength modulation waveform"), and perform the modulation of the laser output power will be referred to as the "laser control unit". The laser control unit 130 provides the modulation of the laser following waveforms (voltages) that can be applied to laser control unit electric inputs ("modulation inputs").

The laser output beam 140 is optically coupled through a mode matching optics set 150 to an optical power buildup cavity (OPEC) 160. A skilled artisan will appreciate that the laser output beam can be a free space beam, or it can be emitted from an optical fiber. The mode matching optics can suitably comprise a number of optical elements, such as lenses, mirrors and/or prisms that transform the laser beam diameter, its divergence and/or its wave front curvature at the OPBC entrance to match corresponding parameters of the OPBC fundamental $TEM_{00}$ mode beam. Various versions of mode matching arrangements are known in the art. In FIG. 1 a collimating lens 151 and a focusing lens 152 are shown as suitable components of the mode matching optics set. The OPBC can be of a variety of types, such as those described in U.S. Pat. No. 7,263,871, and may consist of two or more dielectric mirrors. In FIG. 1 two cavity mirrors, $M_1$ and $M_2$ are shown as illustrating one preferred approach. An optical isolator 155 can suitably be present on the laser beam path before the beam hits the first mirror surface of the cavity. Its function is to reduce the intensity of the optical beam reflected from the cavity back into the laser as such a reflected beam may cause laser instability. There may also be a different use of the optical isolator, and such uses will be described further hereinafter. The optical isolator may be of any suitable type, such as a Faraday Isolator, or a combination of a linear polarizer and a quarter-wave phase plate. These and other types of optical isolators are well known in the art. The first cavity mirror $M_1$ through which the laser beam enters the cavity has its power reflectivity coefficient $R_1$ close to but less than unity, such that the quantity $1-R_1$ is in the range from $10^{-1}$ to $10^{-5}$. The second mirror of the cavity $M_2$ has a power reflectivity $R_2$ equal to or higher than $R_1$. In optical cavities having three or more mirrors, the remaining mirrors will have their power reflectivity $R_3$, $R_4$, etc., preferably as close to unity as mirror manufacturing technology permits. A person skilled in the art will recognize that even high reflectivity mirrors will have some residual transmission, even though it may be as low as several parts per million. The optical coupling between the laser and the cavity is arranged so that the laser oscillating mode electric field distribution is as close as possible to that of the fundamental $TEM_{00}$ mode of the cavity, (which is called "mode-matching"). The mode matching coefficient $\eta$ characterizing the fraction of the laser oscillating mode power that can be coupled into the fundamental cavity mode therefore approaches one. In practice, values of $\eta$ as high as 0.95 are achievable, especially when telecommunication DFB laser diodes with a single mode fiber output are used. A first photo-detector PD is placed behind the mirror $M_2$, which permits one to monitor the power $P_{Circ}$ circulating inside the cavity, because the power hitting its surface $P_{Transm}$ is determined by the Equation $P_{Transm}=P_{Circ} \cdot T_2$ where $T_2$ is the transmission of the mirror $M_2$.

A resonant photo-acoustic cell 165 (PAS cell) is situated inside the cavity in such a way that the optical intracavity beam traverses the resonance element of the cell. The photo-acoustic cell may be of a known type, such as for example that described in U.S. Pat. No. 7,263,871. In another embodiment the photo-acoustic detector is a quartz tuning fork with or without micro-resonator tubes, similar to the one described in U.S. Pat. No. 7,245,380. Such a choice for the photo-acoustic detector within the sensor suggested in the current invention may provide additional benefit of a smaller size. Especially beneficial may be another embodiment within the scope of the current invention where a combination of two or more quartz tuning forks as described hereinafter is used as a resonant PAS cell. In general, it should be clear to a skilled artisan in the field that using other types of photo-acoustic transducers within the cavity described will remain within the scope of the current invention. The amplified output of the PAS cell 165 is connected to a high precision analog to digital converter (ADC) 167, which will be referred to hereinafter as the "First ADC".

If a laser beam is mode matched to the cavity, and one changes its wavelength, the optical power inside that cavity will have a series of resonant peaks (cavity resonances) that are evenly separated as a function of the laser optical frequency $v$. The cavity resonances separation in frequency $\Delta v$ (otherwise known as the free spectral range of the cavity or FSR) can be found as $$\Delta v = c/p, \quad (1)$$

where p is the cavity perimeter. The optical power circulating inside the cavity at the resonance peak $P_c$, will be significantly higher than the incident power (the laser power) $P_i$, and it can be defined by the Equation $$P_c = P_i \frac{\eta T_1}{\left(1 - \sqrt{R_1 R_2}\right)^2}. \quad (2)$$

We will call the quantity $$\frac{\eta T_1}{\left(1 - \sqrt{R_1 R_2}\right)^2}$$

a "buildup factor" which tells one how higher the power circulating inside the cavity is in comparison with the available laser power $P_i$.

If one assume that in a two-mirror cavity both mirrors have equal transmission coefficients $T_1$, $T_2$=1%, and no other losses so that $R_1=R_2=1-T_1=0.99$, and additionally assume a perfect coupling $\eta=1$ and neglect all other losses, such as the much weaker absorption of the sample gas inside the cavity, then from Equation 2 one finds that the buildup factor is equal to 100. Actually, in a two mirror, or in any non-ring cavity, the circulating laser light will go twice through the PAS cell in the middle of the cavity, and thus in this example the effective power that induces the PAS effect will be 200 times higher than that of the laser. With a typical telecom DFB laser power of 20 mW, one gets as much as 4 W acting on the cell.

Having equal reflectivities of the two cavity mirrors seems to be a natural choice, but it is not the best one. If we replace the mirror $M_2$ in this cavity with a higher reflectivity mirror such that $R_2$=0.9999, still with negligible losses so that $T_2$=1-$R_2$=0.01%, the buildup factor will now increase from 100 to about 390 resulting in optical power as high as 15.6 W acting on the intracavity PAS cell. This configuration with the second mirror reflectivity much higher than that of the first mirror is one preferred embodiment.

Figure 3:
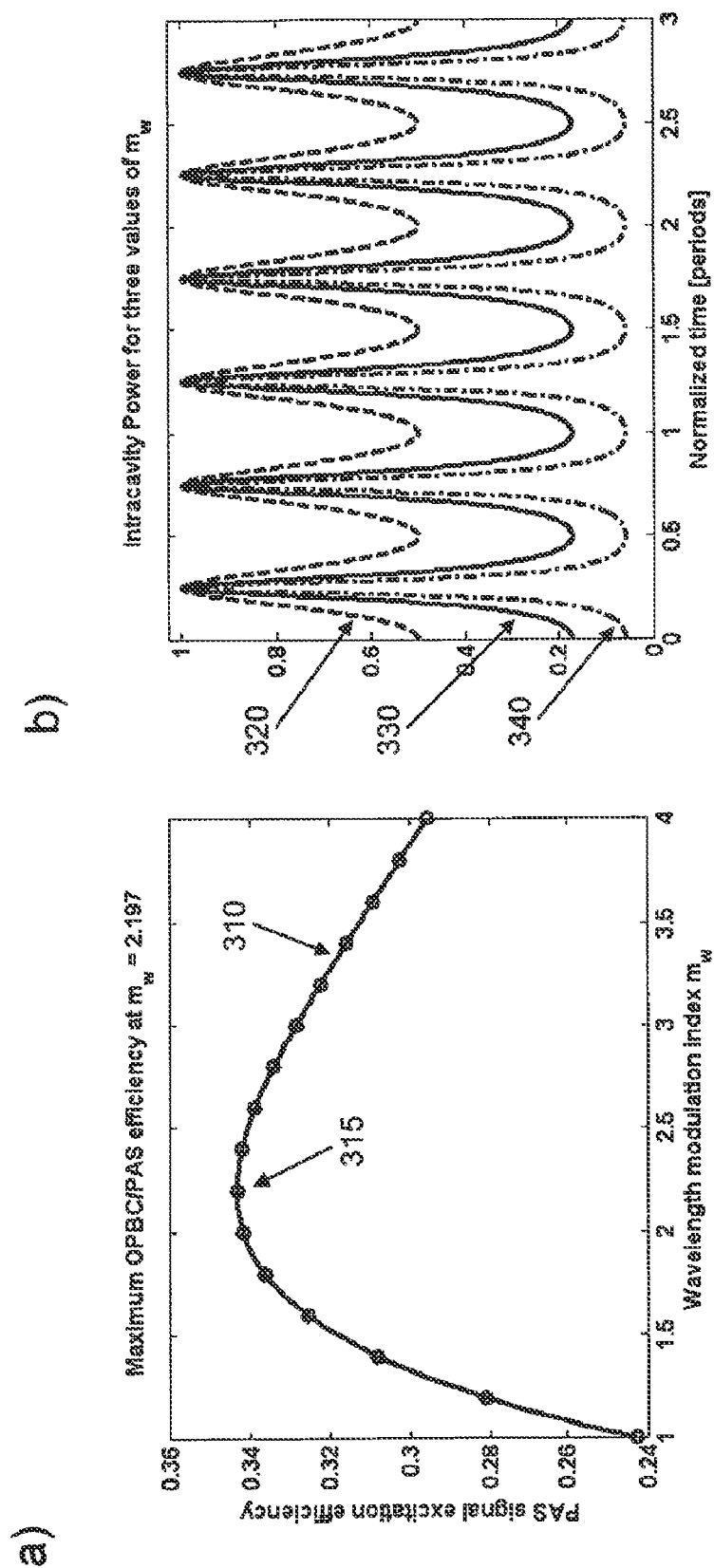
FIG. 3 illustrates the method of the LD wavelength modulation index optimization.

The output power $P_m$ emerging from the second mirror $M_2$ and hitting the photo-detector 170, which will be referred to hereinafter as the "first photo-detector" can be found as $$P_m = P_i \frac{\eta T_1 T_2}{\left(1 - \sqrt{R_1 R_2}\right)^2}, \quad (3)$$

and this power will be equal to 1.56 mW. The output of the first photo-detector 170 is connected to a second high precision analog and to digital converter 175, which will be referred to as the "second ADC". Both the first ADC 167 and the second ADC 175 are connected to a data processing and control unit (DPCU) 180. The DPSU includes one or more data signal processors (DSP), and also has monitor inputs to measure the gas detection system operating parameters, including but not limited to temperature, pressure, ambient air humidity, as well as digital and analog control outputs. The DPSU provides the entire functionality of the gas detection system by running dedicated software. The DPSU functions and operations will be considered in detail hereinafter. As so far described, the sensor configuration might not appear fundamentally different from the prior art systems described previously. However, its significant difference when compared to the prior art systems is that the time average value of the laser operating wavelength remains fixed through the time period of the measurement of a single data point, whereas a large amplitude periodic manipulation is applied to the instantaneous laser wavelength. The term large refers to the full width at the half maximum (FWHM) of the cavity resonance peak, and it designates that peak to peak excursion of the laser wavelength is larger than the cavity resonance peak width, and may thus constitute a significant fraction of the cavity free spectral range (FSR). In the prior art in some embodiments [see, for example, A. Rossi, et. al., (2005), Appl. Phys. Lett., 87, 041110 (2005)] a traditional approach consisted in applying a small amplitude modulation or dither to the wavelength of the laser in order to generate an error signal proportional to the deviation of the laser operating wavelength from the center of the cavity resonance peak. By "small" it is meant that the peak to peak laser wavelength excursion taught in the prior art was a several percent fraction of the cavity resonance peak FWHM. In order to obtain the photo-acoustic signal in the prior art an external chopper was used to periodically interrupt the laser radiation. The perturbations of the lock loop caused by such interruptions make the operation of the loop very unstable and unreliable. One can see such instability in the prior art description shown in FIG. 3. Such instability besides high noise in the PAS signal makes obtaining higher buildup power virtually impossible. The innovative step in the current invention is that the laser radiation is not only uninterrupted, but it does not have to be even amplitude modulated, and yet an efficient amplitude modulation of the intracavity circulating power is achieved. This is accomplished in the current invention by increasing the peak to peak excursion of the wavelength modulation dither waveform to a value larger than the full width of the cavity resonance peak. The intracavity power becomes thereby a series of large amplitude resonance peaks, two peaks for one dither waveform period. The optical power variation within peaks thus may approach 100% of the maximum buildup power thus providing an efficient source for PAS. This two-peak waveform is simultaneously used to generate the uninterrupted error signal. This permits one to achieve a very robust long time lock of the cavity resonance to the laser with an oscillating wavelength, sufficiently robust that the loss of the lock essentially never happens. Even if lock loss happens the system will nevertheless recover it with only a minor delay. This ensures a very robust long time operation of the sensor, and measurement of very small absorption coefficients with an exceptionally good signal to noise ratio not achievable by the prior art systems. The second innovative step of the current invention as compared to the prior art is a further use of said two-peak intracavity power waveform to generate a PAS signal normalization factor which further reduces the noise and makes the sensor response independent of the laser power fluctuations and drifts. This is explained further in the text.

Figure 2:
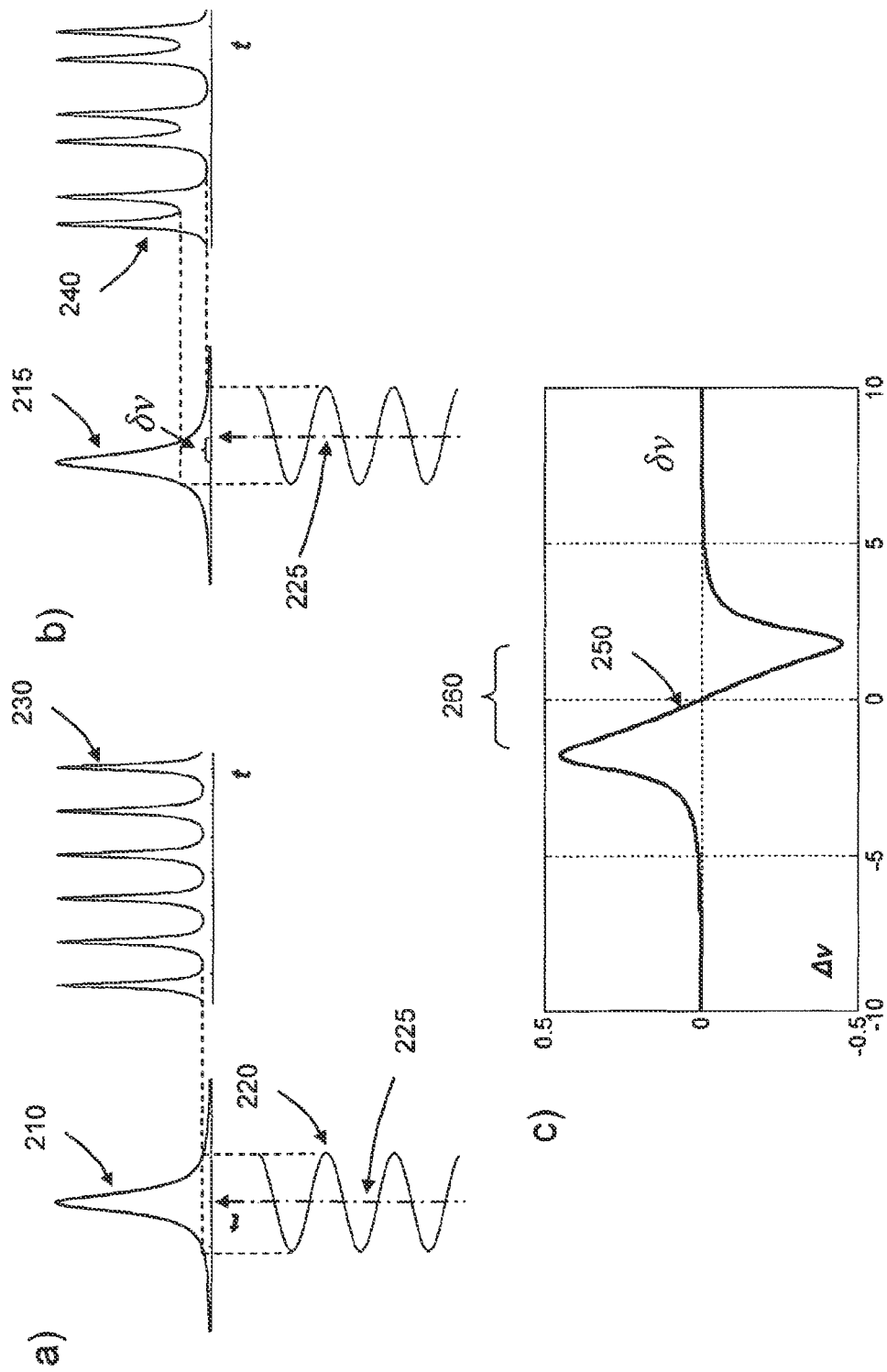
FIG. 2 illustrates the method of locking the laser and the optical cavity in accordance with the present invention by showing the time dependence of the laser wavelength and optical fields inside the cavity for different values of the laser and cavity wavelength mismatch.

The principle of operation of the locking system is illustrated in FIG. 2. If one first assumes that the center optical frequency of the laser coincides with the cavity resonance peak 210 (circulating power within the cavity) as shown in FIG. 2a as a function of the laser optical frequency v. The laser is modulated in wavelength so that its optical frequency time dependence is in the current embodiment sinusoidal, and it can be expressed as $$v(t) = v_0 + \tfrac{1}{2} m_w \sin(2\pi f t), \quad (4)$$

where f is wavelength modulation frequency. The laser wavelength modulation waveform v(t) is generated digitally within the DPSU 180, and converted into an analog electrical signal by a digital to analog converter (DAC) 185 which is an internal part of DPSU 180. The DAC 185 will be referred to as "WM DAC" and its output is connected to the wavelength modulation input 132 of the laser control unit 130. Its time dependence 220 is shown in the lower part of the FIG. 2a with dashed line 225 which indicates both the position of the laser center frequency and also serves as a time axis. The maximum excursion of the laser optical frequency is defined by the modulation index $m_w$, and in the example shown in the Figure the peak to peak optical frequency deviation of the wavelength modulated laser is four times larger than the full width at the half-maximum of the cavity resonance $\delta v_{Cav}$. As a consequence of such wavelength manipulation of the laser the instantaneous laser frequency will pass the cavity resonance peak twice through the modulation period resulting in the time dependence of the intracavity circulating power being a sequence of peaks 230 equally separated in time and having a period twice as short as the laser wavelength modulation period. This time dependence of the intracavity circulating power is shown in the left side of FIG. 2A. As can be seen, one thus obtains an amplitude modulation of the intracavity circulating power as a result of a wavelength modulation of the laser which is advantageously not accompanied with laser intensity modulation at all. If the laser wavelength coincides with the absorption line of a species of interest or analyte molecule, the modulated intracavity power absorbed by the analyte will induce periodic pressure changes within the laser beam thereby providing a photo-acoustic signal. This photo-acoustic signal is proportional to the optical power absorbed by the analyte species and thus to the analyte species concentration.

If for any reason the optical distance between the cavity mirrors should change, resulting in a small shift of the cavity resonance curve with respect to the central wavelength of the laser 225 as shown in FIG. 2b by the curve 215, the time dependence of the intracavity circulating power will now become different from its former symmetric shape 230, and it will become asymmetric as it is shown by curve 240 in FIG. 2b. This asymmetry is a measure of the detuning $\delta v$ of the cavity peak position and the central fixed wavelength of the laser, and the shape shown in FIG. 2b corresponds to the cavity detuning $\delta v$ equal to the cavity resonance peak width $\delta v_{Cav}$. The asymmetry can be determined quantitatively by digital processing the $P_m$ waveform converted into an electrical signal by the first photo detector 170, and digitized by second ADC 175 within DPSU 180. The connections are shown schematically in FIG. 1. Such processing involves the multiplication of the digitized waveform by two sinusoidal functions, the in-phase function $U_X = \sin(2\pi f t + \phi_{WM})$ and the quadrature function $U_Y = \cos(2\pi f t + \phi_{WM})$. The multiplication is done by a DSP within DPSU 180, and the DSP then applies a low pass digital filter to $U_X$ and $U_Y$. The frequency f in $U_X$ and $U_Y$ time dependence, is the same as in the wavelength modulation waveform v(t) 220. The phase term $\phi_{WM}$ in $U_X$ and $U_Y$ has a pre-determined value to zero out the output of the digital filter applied to $U_Y$. This output will be called the quadrature output, or Y-output. The digitally filtered product of $P_m$ and $U_X$ will be called the in-phase output.

The phase term $\phi_{WM}$ plays an important role in the concept of the current invention and thus it will be discussed here in more detail further in the text. For now let us assume that there is already a correct $\phi_{WM}$ value stored in the DPCU memory.

The shape of the in-phase output (X-output) as a function of the cavity peak position detuning $\delta v$ from the central laser wavelength is shown in FIG. 2c for a sinusoidal time dependence of the laser wavelength manipulation, and for wavelength modulation index m corresponding to the laser frequency peak to peak excursion of four times the cavity resonance width. The vertical scale designates the X-output amplitude relative to the peak values of the first photo-detector signal, two examples of which are represented by curves 230 and 240. Output signal 250 has a broad linear part 260 in the frequency interval of about $\pm 2\delta v_{Cav}$. This linear part provides a perfect error signal for the feedback loop that will return the cavity to a precise match with the laser central frequency. This is accomplished by converting the X-output into voltage with a second DAC 187 which is also a part of DPCU 180, and applying this signal to a linear transducer 189 on which one of the cavity mirrors is mounted, as shown in FIG. 1. Positive values of the error signal in FIG. 2c designate that the cavity peak should be moved towards a higher optical frequency, whereas negative values show that the opposite shift should be applied. The fact that the error signal has its peak values as large as almost one half of the peak intensity measured by the first photo-detector means that a very high signal to noise ratio can be achieved in the error signal, and that if the cavity should ever go out of lock, it will relock automatically to the nearest peak. In fact, there is no "dead zone" to re-lock. If the cavity is anywhere within ½ of the free spectral range (FSR) from some peak, it will lock back to this peak. In our experience the relocking after lost lock takes only a few periods of the wavelength modulation waveform.

If the central wavelength position of the laser is now shifted to another wavelength by sending an appropriate signal from DPCU 180 to laser wavelength control input 190, the cavity will automatically follow the laser as long as the cavity lock system is functioning. The PAS signal will now represent the analyte absorption at the new wavelength. This master-slave configuration with the laser being a master that determines the operating wavelength and the cavity being a slave following it thus permits the operator to obtain the dependence of the analyte sample absorption on the laser wavelength (i.e., the absorption spectrum). This will be true as long as the linear transducer 189 that adjusts the cavity mirrors separation through the action of the feedback lock loop remains within its operation range. In a preferred embodiment a PZT is used as such a linear transducer. PZTs usually have a stroke of a few micrometers. This corresponds to several cavity free spectral ranges in the near-IR, but for operation in the mid-IR special attention should be paid to make sure that the stroke is larger than one FSR. In any case, after scanning the central laser wavelength to one or more cavity FSR the PZT limit will be reached and at this moment the system will stop functioning. The scanning range within one PZT stroke will correspond to the spectral interval of about one wave number or even less. This may not always be sufficient to obtain quantitative information about the sample absorption spectrum and thus about the analyte concentration. According to present invention, the spectral range where the absorption spectrum can be recorded can be extended over the entire tuning range of the laser by adding a module to the DPCU which we shall call a "reset module". Such a reset module can be implemented as a part of the DPCU code, or it can be presented by a separate physical structure within the DPCU. The reset module will monitor the approach of the linear transducer 189 to the upper or to the lower boundary of its operating range, and as soon as the linear transducer enters within a pre-determined limit in the vicinity of the boundary, the DPCU commands a stepwise change of the linear transducer position back into its safe operation space. The value of such step is substantially equal to making the cavity length increment or decrement an integer multiple of one half of the laser operation wavelength. The DPCU will also disallow the operation of the cavity locking system and the data acquisition for a fraction of a second while the cavity mirror is being displaced, and then while the locking system regains the lock. Now the thus improved system in accordance with the present invention can make arbitrarily long scans of the sample absorption in wavelength limited only by the tuning range of the laser.

A skilled artisan will definitely appreciate that the described method of injecting the radiation of a laser to a cavity combined with locking the cavity to the laser and thus obtaining inside the cavity the intensity of radiation from several times to several orders of magnitude higher than that of the laser itself is not limited to photo-acoustic spectroscopy, but it can be applied to any other area of application that requires high intensity optical beams. All such applications are therefore within the scope of the present invention. One examples of the application other than PAS that will benefit from the present invention is Raman spectroscopy in liquids and gases, where intense beam at the operation wavelength of a low power diode or other laser can be injected to the cavity thereby providing Raman signal from several times to several orders of magnitude larger than with the laser alone.

Now it is time to discuss the procedure of obtaining a predetermined value of the phase term $\phi_{WM}$. The wavelength modulation waveform v(t) and the functions $U_X$ and $U_Y$ are generated within the same DPCU and they are made totally coherent. The sampling of the second ADC 175 is also made coherent with the dither waveform. If the laser response to the wavelength modulation waveform v(t) were instantaneous, and if there were no amplitude modulation at all of the laser intensity, the quadrature output $U_Y$ would have always been equal to zero, and no such phase term would have been needed. In the real life the laser optical frequency waveform v(t) has always some phase lag with respect to electrical signal on the wavelength modulation input of the laser control unit generated by the WM DAC. Besides, the phase lag the waveform v(t) will certainly have some nonlinear components and the laser wavelength modulation will most certainly be accompanied by an unwanted parasitic laser intensity modulation. This intensity modulation will have its own nonlinear components and its own phase shift. Furthermore the optical cavity itself will introduce some additional phase lag simply because it takes multiple passages within the cavity to build up the injected laser intensity. Finally, the optical absorption within layers of the cavity mirrors and within the intracavity gas may affect both the shape and the position of the intracavity peaks. As a result, the actual signals from the cavity may differ quite noticeably from the idealized case shown in FIG. 2. Fortunately, the impact of all this complexity on the cavity locking process can be significantly reduced by a proper choice of the phase term $\phi_{WM}$. This choice has to be done at the initial setup stage of the sensor, and the procedure is as follows. First one sets $\phi_{WM}=0$, which is not the optimum value, and we then turn the locking system on using the digitally filtered product of $P_m$ and $U_X$ as the error signal. The locking system will still work, even with non-optimal phase unless the correct value of $\phi_{WM}$ turns out to be larger than $+\pi/2$ or smaller than $-\pi/2$. In such case one should make increments to $\phi_{WM}$ equal to $\pi/2$ each time until the lock starts working. Now one scans the laser wavelength within the entire tuning range of the laser and record for the subsequent analysis the digitally filtered products of $P_m$ and $U_X$ as well as of $P_m$ and $U_Y$ alongside with the photo-acoustic signal. Let us call the two sets of said products $I_m$ and $Q_m$. The $I_m$ will be forced to zero by the cavity lock system, but generally $Q_m$ will have non-zero values within the entire scan range. If no absorbing species is present within the cavity, which can be judged by absence of the absorption lines in the PAS signal, $Q_m$ can be rendered to zero within the entire laser wavelength scan by an appropriate choice of the phase term value $\phi_{WM}$. This can be done automatically by repeating scans and making small $\phi_{WM}$ increments until $Q_m$ changes sign, and then finding the best $\phi_{WM}$ value by linear interpolation. This value of $\phi_{WM}$ should be stored within the DPCU memory for future use. The skilled artisan will appreciate that the optimum $\phi_{WM}$ value may slightly change over time because of component ageing, but that small deviations of $\phi_{WM}$ from its optimum value have no effect on the gas detection system performance. Moreover, a revision of the $\phi_{WM}$ stored value can be done by repeating the above procedure during regular maintenance cycles of the system.

The procedure may get a little more complex in case some absorbing gas is present within the cavity. In such case the photo-acoustic signal will have some absorption lines in it. We observed that the $Q_m$ signal will then have peaks strongly correlated with the absorption lines present in the photo-acoustic spectrum, even in case when the optimum $\phi_{WM}$ has been found and set. We believe that this is due to the instantaneous effect of the changes of the refractive index of the intracavity medium due to the optical absorption. We recognize that this effect alone may become a new method of the sensitive absorption spectroscopy, and a subject of a separate invention, but it will be discussed elsewhere. For the purpose of the present invention it is sufficient to say that in case the absorption peaks are present in the scan, the data points of $I_m$ and $Q_m$ that are within and in the vicinity of such peaks will be excluded in the procedure of finding the optimum $\phi_{WM}$.

We now describe in detail the procedure of obtaining accurate information about sample absorption. The wavelength manipulation applied to the laser as described above with a functioning cavity to laser lock system results in the sequence of peaks of intracavity circulating power as is shown by the waveform 230 in FIG. 2. There are two peaks for one wavelength manipulation period, and the peaks are equidistant in time domain. They will therefore produce periodic expansion and contraction of the intracavity gas known as photo-acoustic excitation at a frequency fs=2f. This will result in a resonant excitation of the PAS cell under the condition that the frequency of the laser wavelength manipulation f is made ½ of its resonance frequency. The electrical output of PAS cell 165 is connected to the first ADC 167, and the digitized waveform of the first ADC will be multiplied within DPSU 180 by two sinusoidal functions, the in-phase function $U_{XS}=\sin(2\pi f_S t+\phi_S)$ and the quadrature function $U_{YS}=\cos(2\pi f_S t+\phi_S)$. In accordance with current invention the two pairs of functions $[U_X, U_Y]$ and $[U_{XS}, U_{YS}]$ are generated from the same clock so that they are coherent. Moreover, in accordance with current invention, the sampling clock of the first ADC is identical with the sampling clock of the second ADC, and as we already pointed out, it is derived from the same master clock as the frequency modulation waveforms. A skilled artisan will appreciate that the filtered products $I_S=f_S \times U_{XS}$ and $Q_S=f_S \times U_{YS}$ will represent the fraction of the circulating intracavity beam power $P_c$ at the frequency $f_S$ absorbed by the analyte. Now with the locking system in operation scanning the laser wavelength in the pre-determined range will produce the sequence of pairs $I_S$ and $Q_S$, each pair containing the information of optical absorption spectrum of the intracavity species. They are proportional to each other, and their ratio depends on the phase term $\phi_S$ in the waveforms $U_{XS}$ and $U_{YS}$. The preferred choice of the phase term $\phi_S$ is one that zeros out the quadrature component of the first ADC at twice the laser wavelength dither frequency. This preferred choice value of the term $\phi_S$ can be and should be determined at the stage of the initial setup of the apparatus and stored within the DPCU for use in future cycles. The procedure for such determination is as follows:

Each pair of these products values can be considered as components of a vector in a Cartesian coordinate system. The application of the coordinate rotation transformation by an angle $\phi$ to the both sets will give two new sets of values $I_S$ and $Q_S$ with the new phase term $\phi_{SNew}=\phi_{SOld}+\phi$. It is sufficient to make on the initial setup stage one scan of the laser within the entire pre-determined tuning range with any initial value of the phase term $\phi_S$, then find the value of the rotation angle $\phi$ that zeros down the quadrature component $Q_S$, and stores the sum $\phi_S+\phi$ in the DPCU as the best value of the phase term. Such determination should be done after the best value for the phase term $\phi_{WM}$ has been found. As soon as a correct value of the phase term $\phi_S$ has been applied, the in-phase component of the first ADC signal $I_S$ at twice the wavelength dither frequency will represent the wavelength dependence of the intracavity absorption.

At this point we have taught how with a low power laser by injecting its radiation into an optical cavity one can obtain hundreds or thousands times higher power which is modulated in amplitude, and can thus induce a hundred or thousand times larger photo-acoustic signal. We have also taught how to maintain the best conditions for such injection by locking the cavity resonance to the laser and reliably maintaining such lock for indefinitely long periods of time. Finally, we have taught how to maintain the lock while scanning the laser in an arbitrarily wide spectral range, and how to obtain the absorption spectrum of the filling cavity medium from this scan.

In accordance with present invention, several preferred features as described below will further enhance the sensor performance and its measurement accuracy. As has been already pointed out, the time dependence of the power $P_c$ circulating within the cavity under normal operation of the cavity lock loop has the form of a sequence of peaks as is shown in FIG. 2a, curve 230. The PAS cell output is proportional to the sample absorption at the laser central wavelength, but it also depends on the peak to valley ratio of the circulating power peaks as well as upon the particular shape of these peaks. More precisely, a normalizing factor can advantageously be applied to each value of the signal pair $I_S$ and $Q_S$ that represent the intracavity PAS cell output to make this signal truly proportional to the sample absorption. This normalization factor is a Fourier-component of the actual time dependence of $P_c$ at the frequency $f_S$ equal to the detection harmonics of the signal. The signal of the first photo-detector 170, already digitized by second ADC 175, is used to obtain this normalization factor by its additional processing within DPCU 180. This processing comprises the multiplication of the digitized time dependence of $P_c$ by two sinusoidal functions again, the in-phase function $U_{XN}=\sin\backslash(2\pi f_S t+\phi_N)$ and the quadrature function $U_{YN}=\cos(2\pi f_S t+\phi_N)$. The frequency $f_S$ in these functions is the same as the frequency used for the processing of the PAS cell output, and it is twice as large as the frequency f of the wavelength modulation of the laser. The filtered products $I_N=f_S \times U_{XN}$ and $Q_N=f_S \times U_{YN}$ represent the normalization signal in the same way as the quantities $I_S$ and $Q_S$ represent the PAS signals. By analogy with the PAS signals the phase term $\phi_N$ can be set to its optimum value that zeroes down the quadrature normalization component $\phi_N$. A skilled artisan will appreciate that the same procedure as just described for the PAS signals will be applied at the initial setup stage of the sensor, and the optimum $\phi_N$ value will be determined and stored in the DPCU memory for future use.

Once the optimum value of the phase term $\phi_N$ has been set, the normalization involves the division of the signals $I_S$ and $Q_S$ by the corresponding value of $I_N$. Such normalization eliminates the variation of the amplitude and shape of the intracavity power dependence on time due to the laser and cavity ageing as well as to operation of the cavity locking system onto the PAS signal measurement result. After the normalization the PAS signal becomes truly proportional to the optical absorption spectrum. The proportionality coefficient becomes a calibration constant of a particular instrument can and is determined at the initial setup stage by recording the spectrum of a calibration analyte sample with a precisely known concentration and stored in the DPCU memory.

The fact that we are measuring value of the in-phase component of the first photo-detector signal at the second harmonic of the wavelength dither frequency $I_N$ offers an additional opportunity to further improve the reliability of the long term sensor operation. In accordance with the present invention we introduce a method of verification that the cavity is in the locked position. If the cavity resonance peak is locked to the laser, the signal $I_N$ will be at its maximum. At the initial setup stage while the laser wavelength scan in the entire laser tuning range is performed, one stores the set of $I_N$ values as a function laser operation wavelength within DPCU. Then at the stage of regular operation before the measurement of the normalized PAS signal, one verifies that the ratio of the measured current value of $I_N$ to the stored $I_N$ value at the current laser operating wavelength is not lower than a predefined threshold value, which signifies that the cavity resonance peak is still locked to the laser. If this is not the case, the data acquisition is temporarily suspended and the re-locking procedure is initiated. The relocking involves sending to the moveable mirror assembly a command to perform a linear mirror position ramp until the current $I_N$ to the stored $I_N$ ratio again becomes higher than the threshold value. Then the data acquisition is re-established. The predefined threshold can be any value higher than 0.9 but lower than 1.0.

As soon as one wavelength scan in the pre-determined wavelength range has been completed, and the absorption spectrum of the intracavity gas has been determined, one or more analyte species can be identified and their concentration found by established procedures known in the art.

In one of the embodiments of the present invention the laser operation wavelength is kept at the maximum of the analyte's absorption line, and the normalized filtered product $I_{SN}=I_S/I_N$ continuously provides the sample absorption change as a function of time. The cavity to the laser lock loop and the reset module will provide continuous seamless operation of the sensor in this mode as well. The reset module will come into action whenever the ambient conditions have changed to the extent that the linear transducer approaches a margin of its operating range in its attempt to compensate for the ambient conditions change effect.

A person skilled in the art will certainly recognize that the method of phase sensitive detection of periodic signals by low-pass filtering the products of these signals by in-phase and quadrature sinusoidal functions matches the description of a digital data signal processor (DSP) based lock-in amplifier (LIA). This observation is correct and the functions described above can be realized by a combination of three general purpose digital lock-in amplifiers, the signals of which will be processed by a simpler DPCU. There exists many reasons however, that make the approach described in the present invention preferable. One reason is that our solution is far less expensive and substantially more compact. The signal of the first photo-detector is first processed by a LIA at the first harmonic of the laser wavelength modulation frequency for the locking purpose, and the same signal will need to be processed by another LIA at the second harmonic in order to give the normalization signal. The cavity locking to the laser will have to be performed by the third LIA. Besides the fact that the multiple LIA approach is really wasteful, the accuracy of the normalized absorption signal will in such case be noticeably worse. The reason is that each standalone LIA has its own sample clock that has to be synchronized with the external modulation (dither) signal by an internal phase-locked loop. The three LIA will have three phase-locked loops, each with its own phase jitter. Thus the sampling of the PAS signals, and of the first photo-detector signals at the first and at the second harmonic of the modulation frequency will occur at different times. This negatively impacts the mutual noise between the PAS channel and the normalization channel, and thus the normalization accuracy. Furthermore the laser wavelength modulation waveform then has to be generated by an external direct digital synthesizer (DDS) with its own clock which is again not synchronized with the any of the three sample clock generators in the three separate stand alone LIA. This will additionally introduce a beat noise between the LIA sample clock and the DDS clock.

A DSP based with a single clock that drives both the first and the second ADC as well as dither waveform DDS makes all sampling events truly synchronous, and by definition avoids any beat phenomenon between the ADC sampling and the dither.

Finally, several comments can be made about using analog LIA versus digital LIA in the practice of the present invention. The use of an analog LIA for cavity locking can sometimes presents certain advantages versus a digital LIA because digital processing will cause additional delay that may negatively impact the rapidity of the locking system response. However, in a preferred embodiment of the current invention the cavity is very compact, and consequently it is not sensitive to external perturbations. In other words, the cavity will going out of resonance with the laser in case the feedback loop has been disabled, rather in the form of a slow drift than a fast run out. The rapidity of the cavity lock loop is then not a crucial factor for this method. In contrast, the normalization with an analog LIA may have lower performance as compared with a digital LIA. The reason is that in an analog LIA the signals are multiplied by a square wave (chopped) in contrast to multiplication by a sinusoidal wave in a true digital lock-in. The product will then have a contribution from higher order harmonics. As the harmonics content of the PAS cell signal and the signal of the first photo-detector are not the same, this will reduce the accuracy of normalization. In summary, the use of analog lock-in amplifiers in the PAS channel and in the normalization channel is not preferred regardless of the fact that it may produce reasonable looking spectra.

The gas detection system described above represents a preferred embodiment of the present invention. The system described is functional, and permits one to measure weak absorption in gases with high accuracy, stability and sensitivity.

Additional features of the present invention will now be described. They further disclose the principle of operation of the gas detection system and additional ways to increase its performance. A very useful feature of the sensor according to the current invention is that it naturally allows the locking of the laser operation wavelength to the analyte absorption line of interest. Even though contemporary semiconductor DFB lasers are relatively stable, their operating wavelength corresponding to any fixed setting of the laser operating temperature and current may drift as a function of time due to ageing, as well as to changes in ambient conditions. Such drift, usually a fraction of a nanometer, may be too large as compared to the narrow absorption lines of some analyte species of interest, and it may degrade sensor accuracy. It is especially important for sensors that continuously operate at the absorption line peak, and this is why locking the laser to the absorption peak is required. Doing this in other versions of the OPBC enhanced PAS, for example the one described in A. Rossi, et. al., (2005), Appl. Phys. Lett., 87, 041110 (2005) is not easy for the same reason as locking the cavity to the laser.

The OPBC enhanced amplitude modulation PAS with a wavelength modulated laser sensor architecture provided by the current invention offers an opportunity for laser wavelength ageing drift compensation. This is accomplished by splitting out a small fraction of the DFB laser power (normally not more than a few percent) and directing it to a second photo-detector through a wavelength reference. In a preferred embodiment such a wavelength reference is a small absorption cell filled with the analyte gas of interest at a higher concentration, but it can as well be a narrowband optical filter, such as a solid-state Fabry-Perot etalon or volume Bragg grating. The fact that the laser wavelength of the amplitude modulated PAS system of the present invention is periodically varied, allows one to use wavelength modulation spectroscopy as a tracking tool to determine if and how far the laser has deviated from the reference wavelength, and to lock the laser to such a reference wavelength. This is accomplished by connecting an additional LIA ("a wavelength reference LIA") to the output of the second photo-detector operated at the first, the third or other odd harmonic of the laser wavelength dither frequency f. The laser can now be locked to the wavelength reference peak by methods known in the art.

In the description of the basic principles of the current invention it has already been explained that a wavelength modulation with an amplitude larger than the cavity resonance peak width is applied to the laser, and that such wavelength modulation results in high-depth amplitude modulation of the laser field inside the cavity. The method of determining the optimum laser modulation amplitude (laser wavelength dither amplitude or modulation index) in a preferred implementation of the gas detector will now be explained. The key parameter for this method is maximization of the PAS cell response.

In FIG. 2a, curve 230 shows the time dependence of the intracavity power for a particular value of the modulation parameter m, namely for m=2 for the case when the cavity is locked to the laser and δv~0. The periodic change of the gas pressure due to the heat absorbed by the analyte molecules will induce the output signal in the PAS cell, which as has been explained will be processed within DPCU 180 in the way already explained to produce signals $I_S$ and $Q_S$. This signal will depend on the particular shape of the intracavity power time dependence 230, and will be proportional to the output signal IN derived from the second harmonic of the cavity dither frequency of the first photo-detector output signal. The method of optimization of the wavelength modulation index m, in accordance with the present invention can be realized as follows:

Apply wavelength modulation with the modulation index m close to one. The particular choice of the m value is not critical.

Activate the locking system of the cavity to the laser and observe the normalization signals $I_N$ and $Q_N$. Henceforth, all operations will be performed with the locking system active, which will maintain the symmetric shape of the intracavity power peaks as is shown by curve 230.

Adjust the phase of the normalization signals $\phi_N$ to zero down the Y signal. Doing this will bring the $I_N$ signal to its maximum value for a given wavelength modulation factor m.

With the locking system in operation, optimize the modulation index m by changing the wavelength modulation amplitude until the maximum value of the $I_N$ signal is reached. This will provide the optimum value of the wavelength modulation index m resulting in the maximum PAS cell output under the current operating conditions. A skilled artisan will understand that this can be done automatically by the DPCU.

Once the optimum value of the wavelength modulation index has been found, the DPCU will periodically keep optimizing the modulation index, thus taking into account the components ageing.

An example of such optimization is shown in FIGS. 3a and 3b. Curve 310 in FIG. 3a shows the PAS signal excitation efficiency as a function of the wavelength modulation index $m_W$. It reaches its peak 315 at $m_w$=2.197. The PAS signal excitation efficiency at the peak for sinusoidal wavelength manipulation of the diode laser is 0.343. FIG. 3b shows the time dependence of the intracavity power normalized to its peak value for three values of the modulation index $m_w$. Dashed line 320 corresponds to $m_w$=1, solid line 330 represents the optimum value of $m_w$=2.197, and finally dash-dot line 340 is for $m_w$=4. This Figure provides an intuitive understanding why PAS signal excitation efficiency is lower for two marginal values of $m_w$. A person skilled in the art will know that in PAS with amplitude modulation the PAS signal excitation efficiency is equal to 0.5 for the sinusoidal shape of the intensity modulation function. Curve 320 looks very close to a sinusoidal shape, but the modulation depth is only 50%. Then the PAS signal excitation efficiency should be, and indeed it is, close to 0.25. In contrast to that, curve 340 shows the largest modulation depth, but the peaks are too narrow. Curve 330 represents the best compromise i.e., the modulation depth is not too low and the peaks are not too narrow.

In a gas detection system according to the current invention the LD wavelength manipulation waveform is produced digitally within DPCU 180, and this digital waveform is converted into analog modulation signal by WM DAC 185. Traditionally in wavelength modulation spectroscopy a sinusoidal modulation functions was used. In accordance with present invention we would like to point out that it does not need to be sinusoidal but can be of any periodic shape. In the present apparatus based upon a DSP any waveform can be stored in the DDS memory and then sent to the output. According to the present invention we are going to give examples of non-sinusoidal periodic wavelength modulation waveforms, and to demonstrate how a non-sinusoidal laser wavelength manipulation waveform can be optimized to give a better PAS signal excitation efficiency with the additional advantage of increasing the cavity to laser lock range.

Figure 4:
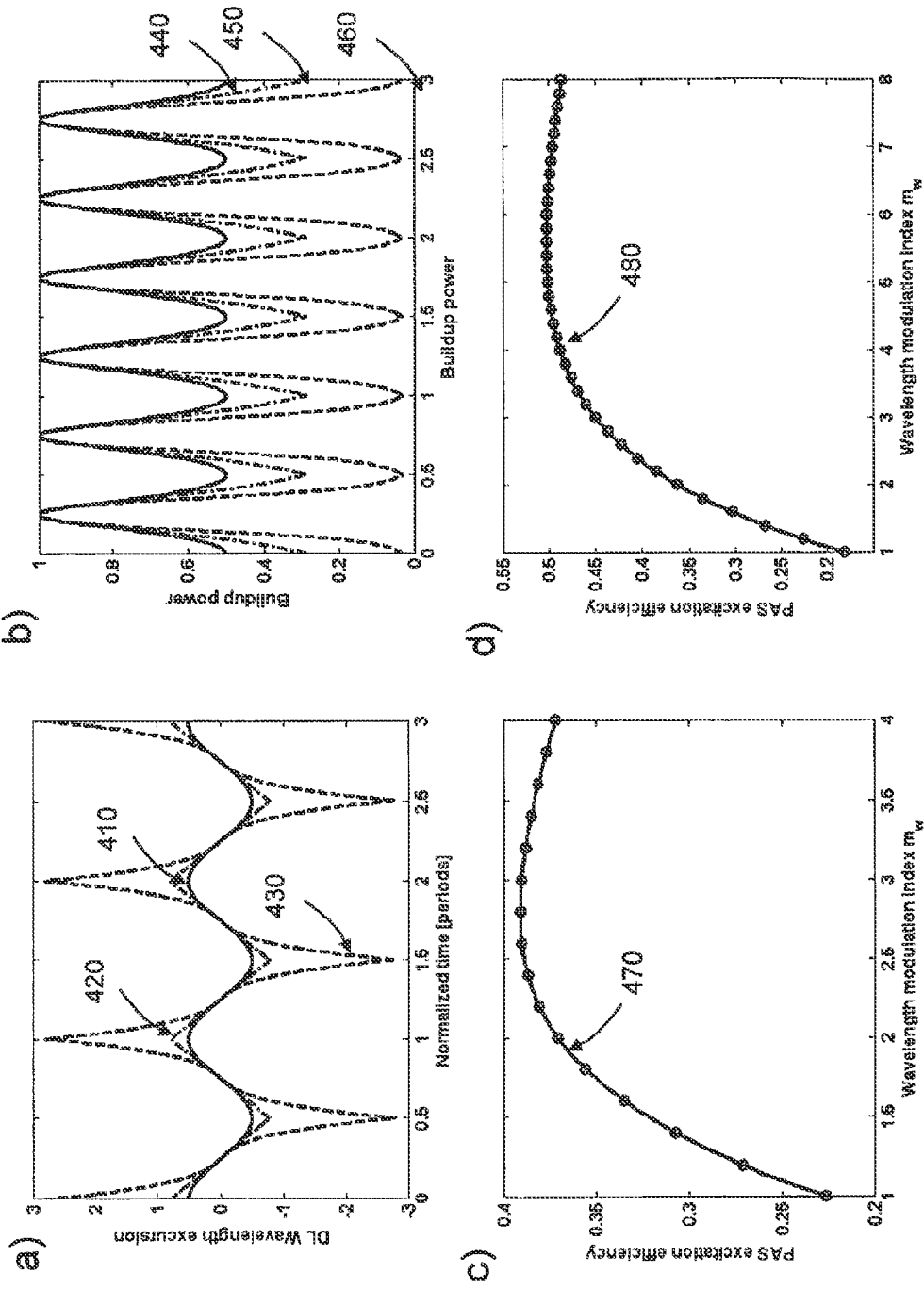
FIG. 4 illustrates the LD wavelength modulation-time dependence that provides a better PAS signal excitation efficiency than does traditional sinusoidal modulation.

As has been already described, the PAS signal excitation efficiency can be increased by making the modulation depth larger and at the same time keeping the intracavity power peaks wider. To further illustrate this embodiment, three Diode Laser wavelength modulation waveforms are shown in FIG. 4A. Waveform 410, shown by the solid line, is a sinusoidal wavelength modulation with a modulation index $m_w$=1. The second waveform 420 (shown by the dash-dot line) has saw-tooth time dependence. By analogy with the sinusoidal function, we designate this waveform as $v(t)=v_0+\frac{1}{2}m_w\text{saw}(2\pi ft)$ so that the saw-tooth modulation with a modulation index $m_w$=1 will have peak to peak swing equal to one FWHM of the cavity resonance peak. Waveform 420 has a modulation index value of 1.57, such that its slope at zero crossing is equal to that of the sinusoidal function. Finally, the third diode laser modulation waveform 430 (shown in FIG. 4a by a dashed line) can be described by a function as $$v(t)=v_0+\tfrac{1}{2}m_W[a\square\mathrm{saw}(2\pi ft)+(1-a)\square\mathrm{saw}^3(2\pi ft)]. \quad (4)$$

With a modulation index $m_w=5.6$ this third waveform has the same slope at zero crossing as the sinusoidal function, but a much higher slope close to its peaks. The sharpness of the peaks is controlled by the "sharpness" parameter a, which in the case shown is equal to 0.25.

By referring to FIG. 2a and replacing the sinusoidal wavelength modulation function 210 by one of the curves 420 or 430 one readily understand how the intracavity power time dependence will change when these waveforms are used. Three intracavity power time dependences corresponding to waveforms 410, 420, and 430 are shown in FIG. 4b by corresponding curves 440, 450, and 460. Waveform 460 has the largest modulation depth, and the ratio of the intracavity power peak width to the time interval between peaks is about ½. A skilled artisan would expect the maximum PAS excitation efficiency for the third waveform to be the largest among the three waveforms and to approach its maximum value of 0.5

Figure 5:
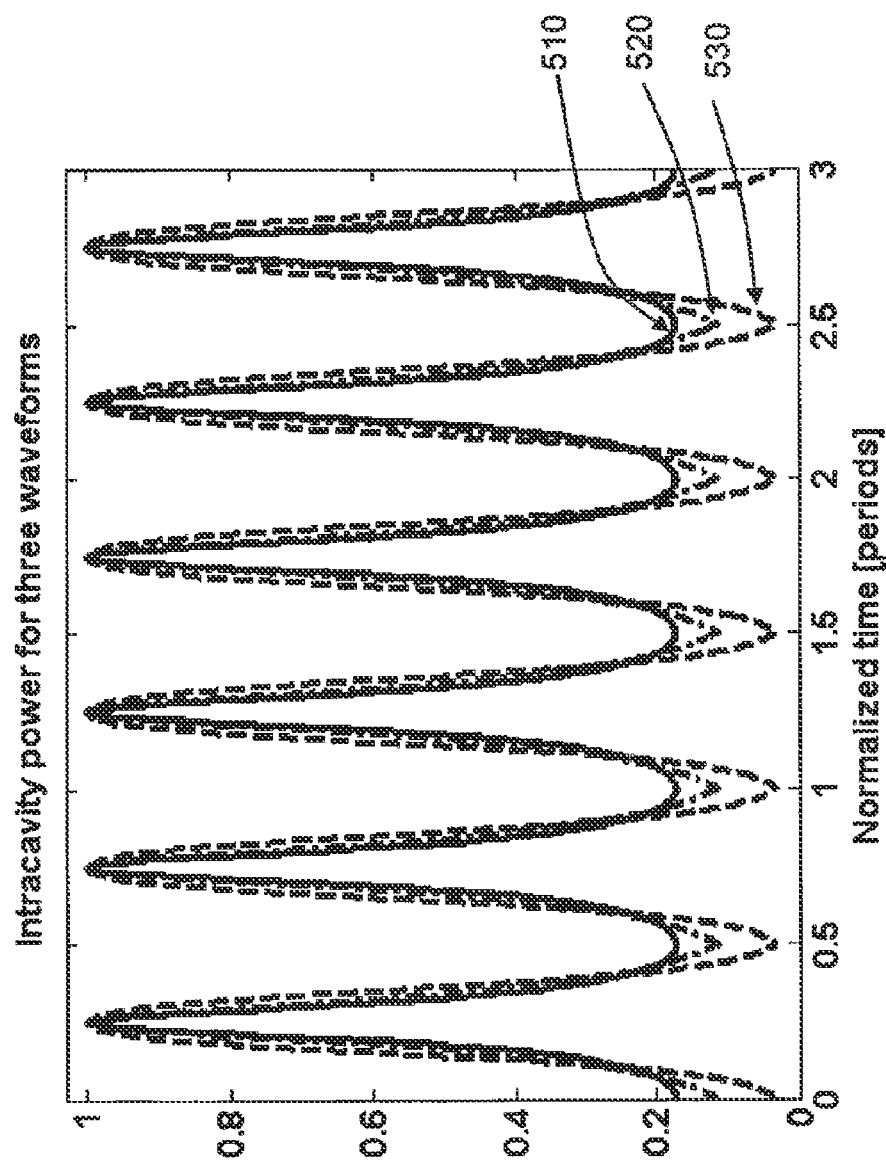
FIG. 5 illustrates the time dependence of the optical power within the OPBC for three special wavelength modulation waveforms.

Indeed, in FIGS. 4c and 4d, showing the dependence of PAS excitation efficiency on the wavelength modulation index for the saw-tooth waveform 470 and for the special waveform 480, respectively, one can see that the maximum PAS excitation efficiency of 0.5 is reached with special waveform 480 at the $m_w=5.59$. The maximum PAS excitation efficiency for saw-tooth waveform 470 is also higher than for the sine excitation and its peak value is 0.391 at $m_w=2.79$. FIG. 5 further shows the effect of the laser diode wavelength modulation waveform change. Three curves in FIG. 5 show the intracavity buildup power as a function of time for the three kinds of the wavelength modulation, all taken at the value of the wavelength modulation index that brings PAS excitation efficiency to a maximum. Solid line 520 shows the intracavity power for sinusoidal modulation, dash-dot line 520 for saw-tooth modulation, and dashed line 530 corresponds to the special modulation waveform. A skilled artisan will recognize that the special modulation waveform has been given as a function described by equation (4) only as an example. The important feature of the special laser diode wavelength modulation waveform is that its slope is at its minimum near zero crossing in the area where the laser wavelength crosses the cavity peak, and it has a larger slope outside the cavity resonance peak area. This can be accomplished with a variety of functional forms, or it can be given as an interpolation of several tabulated values. All these alternatives are within the scope of the present invention.

Figure 6:
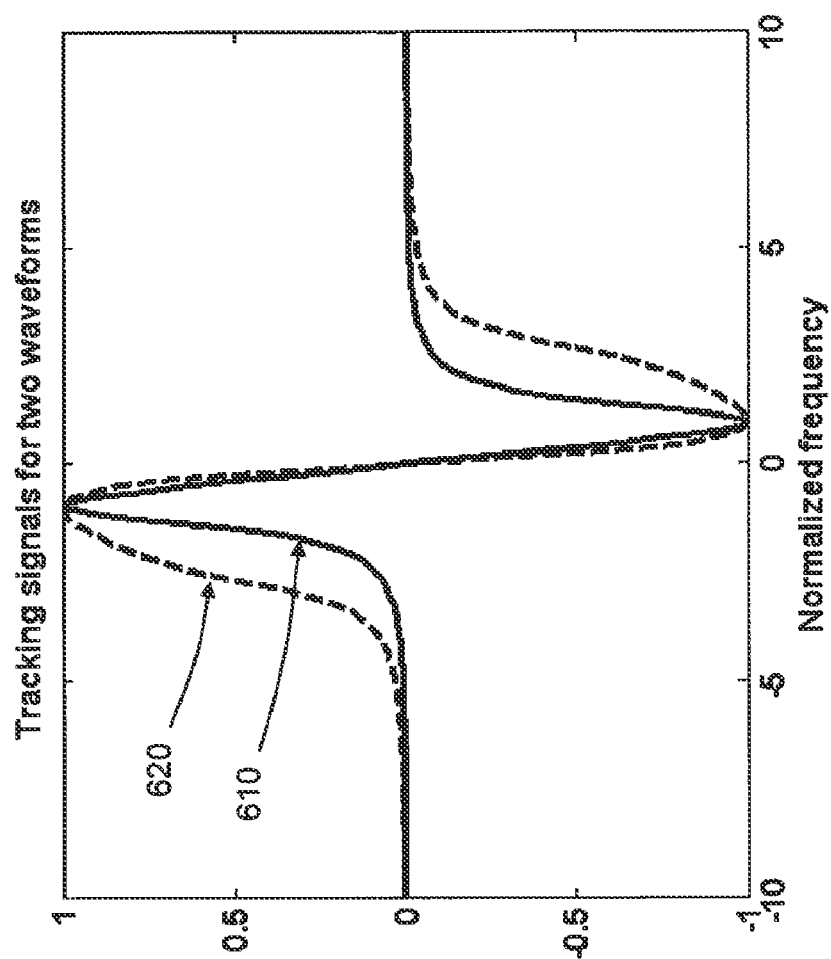
FIG. 6 illustrates the advantage in the cavity locking range with a special modulation waveform

Besides increasing the PAS excitation efficiency nearly 1.5 times, from 0.343 to 0.5, the application of the special modulation waveform has an additional positive effect, namely the locking range of the cavity to the diode laser increases. In FIG. 6 trace 610 shows the normalized error signal that is used to lock the cavity to the laser for the case when the laser wavelength modulation waveform has a sinusoidal shape. Trace 620 corresponds to the special modulation waveform. With special modulation the full width at the half-maximum of the error signal peaks is 2.25 times larger, which indicates a correspondingly larger locking range and higher immunity of the lock to external perturbations.

The gas detection method in accordance with present invention has certain requirements for the mutual values of the laser and cavity parameters that should be taken into account. As has been already described, the laser wavelength is periodically swept around the cavity resonance peak with the sweep frequency being equal to one half of the PAS cell resonance frequency. A first limitation comes with respect to the sweep speed. If one assumes that the laser line width is much narrower that the resonance peak width of the cavity, then indeed the time dependence of the intracavity laser power will follow the shape of the cavity peak as the laser wavelength is being tuned across the peak. However, sweeping the laser too fast can make the injection of the laser power into the cavity less efficient. The criterion of whether the scanning is or is not too fast, comes from a comparison of the time that it takes for the laser wavelength to cross the cavity peak width, and the decay time of the laser radiation inside the cavity.

The cavity resonance peak full width at the half-maximum, $\delta v_{Cav}$ expressed as the laser optical frequency can be found from the resonant cavity length $L_c$ and the reflectivities of the mirrors as:

$$\delta v_{Cav} = \frac{\Delta v_{Cav}}{F}, \quad (5)$$

where $$F = \frac{\pi^4 \sqrt{R_1 R_2}}{1 - \sqrt{R_1 R_2}}$$

is called cavity finesse, and $$\Delta v_{Cav} = \frac{c}{2L_c},$$

is the frequency interval between the subsequent cavity resonance peaks which is called the cavity free spectral range ("FSR"). The value of the decay time $\tau_{Cav}$ of the laser radiation inside the cavity also depends on the cavity length and the minor reflectivity as $$\tau_{Cav} = \frac{L_c \sqrt{R_1 R_2}}{c(1 - \sqrt{R_1 R_2})}. \quad (6)$$

With the laser optical frequency being swept one sees the effects of the cavity finite response to its excitation when the time $\tau_{\delta v}$ of the laser frequency passage through the cavity full resonance width approaches the cavity decay time $\tau_{Cav}$. For convenience in considering these transient effects, analysis we introduce a scanning speed parameter $\xi_{WM}=\tau_{Cav}/\tau_{\delta v}$.

Figure 7:
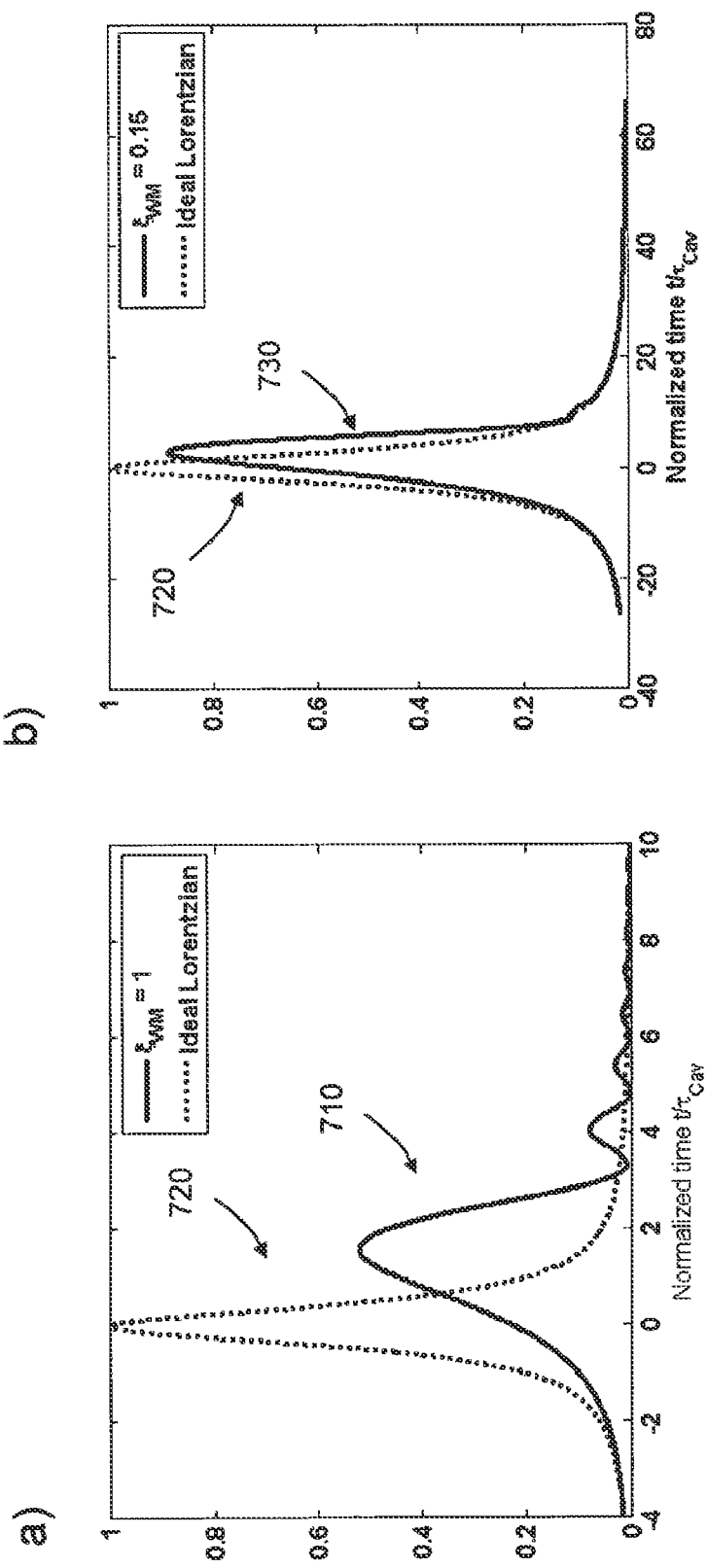
FIG. 7 shows ringing effects when the laser wavelength is being swept across the cavity resonance with different sweep speeds

One may expect that the limiting value for the scanning speed parameter should be close to $\xi_{WM}=1$. The time dependence of the intracavity circulating power calculated for such scanning speed is shown in FIG. 7a, by solid line 710. The idealized Lorentzian response is shown by dotted line 720. Curve 710 not only demonstrates reduced injection efficiency, but it also manifests significant ringing and delay, which would make the operation of the cavity locking system to the laser difficult. The scanning should therefore be slower. The border scanning speed parameter value in accordance with the present invention is $\xi_{WM}=0.15$. For such a scanning speed, the ringing and the peak delay are at an acceptable level, and the injection efficiency is only reduced ~11%.

As an example let us consider a cavity with a length $L_c$=10 cm which is capable of accommodating a typical 6 cm long PAS cell. If one also assumes the same reflectivity $R_1$=$R_2$=99% and therefore negligible losses for both cavity mirrors, such a cavity will have a buildup factor of 100, a finesse F=312.6, a resonance peak width $\delta v_{Cav}$=4.96 MHz, and a decay time $\tau_{Cav}$=33.0 ns. If one couples only 10 mW of the laser power into the cavity, one obtains a circulating power of 1 W. If one further assumes that a saw-tooth modulation waveform is used at the optimum value of $m_w$=2.79, the time $\delta_{\delta v}$ of the laser frequency passage through the cavity full resonance width will be a half-period of the PAS cell resonance frequency of 2600 Hz divided by $m_w$, which gives $\tau_{\delta v}$=276 µs, and it is thus three orders of magnitude slower than the cavity decay time $\xi_{WM}$=1.2×10$^{-4}$.

Such a value of $\delta_{WM}$ indicates that as far as the cavity response is concerned, one could increase the mirror reflectivity about 1000 times and get a 1000 times bigger power buildup. By taking $R_1$=$R_2$=99.999% one gets F=3.1×10$^5$, $\delta v_{Cav}$=4.8 kHz, and $\tau_{Cav}$=33.3 µs. Keeping the same value of the wavelength modulation index $m_w$=2.79 means that the actual laser wavelength peak to peak stroke is now 1000 times smaller than in the previous example. Now $\xi_{WM}$=0.12, which is quite close to the limiting value, and with 10 mW coupled into the cavity one gets an impressive 1 kW of intracavity circulating power.

Mirrors with losses of less than 10 ppm are commercially available, and buildup factors very close to 10$^5$ can be obtained as will now be shown.

We have already described the limitation on the cavity parameters that results from a maximum acceptable scanning speed, and have further demonstrated that this kind of limitation allows an intensity buildup as high as 10$^5$. A limitation comes from the relation between the cavity and the laser line width and may in some cases arise before the already described limitation starts to take effect.

So far the analysis of the gas detection system operation has been done with the assumption that the laser linewidth $\delta v_{Las}$ is significantly smaller than the cavity resonance width $\delta v_{Cav}$. This condition can be easily satisfied for short cavities and small intensity buildup factors. However, a skilled artisan will note that increasing the cavity length in order to accommodate larger PAS cells, and/or increasing the cavity mirrors reflectivity with the intent to achieve higher circulating power inside the cavity may lead to the situation when $\delta v_{Las}$ approaches $\delta v_{Cav}$. If one keeps increasing the mirror reflectivity, this will lead us from a situation where $\delta v_{Las}$<<$\delta v_{Cav}$, when the intracavity power adiabatically follows the cavity resonance profile to the situation when $\delta v_{Las}$>>$\delta_{Cav}$. At this limit the expressions (2) and (3) are no longer valid and transient cavity response functions as well as the model of a laser with phase noise should be used to understand the system behavior. The situation when the laser is much broader than the cavity resonance is typical in Cavity Ring-Down Spectroscopy (CRDS), and the analysis of this situation including the passage of the laser optical frequency through the cavity resonance as has been described in the prior art. It is important to know that the laser linewidth is determined by the phase noise of the laser electric field induced by random spontaneous photons driving the field out of phase with itself in a diffusion-like process. As a result, the laser spectrum can be thought of as a monochromatic wave with its phase drifting in time. This phase drift can be interpreted as the laser random frequency drift within the laser specified linewidth.

This means that instead of a smooth laser wavelength modulation wave form 220 as shown in FIG. 2, one has to assume a random laser frequency fluctuation superimposed on that waveform. The spread of that random frequency fluctuation is the laser linewidth. As a result, even in the area $\delta v_{Las}$<<$\delta v_{Cav}$ the cavity buildup traces may not be as smooth as shown in curve 230, but will have some noise. The visibility of this noise depends upon relative magnitude of $\delta v_{Las}$ and $\delta v_{Cav}$.

$\delta v_{Las}$ is determined by the laser properties, or more precisely, by the coherence time $\tau_{Ph}$ of its radiation phase randomly driven by spontaneous emission. The coherence time means that within this time the phase Φ(t) the lasing mode will drift on average one radian out of its initial value. The laser linewidth can be expressed from its coherence time as $$\delta v_{Las} = \frac{1}{2\pi \tau_{Ph}} (1 + a^2), \quad (6)$$

where a is the "linewidth enhancement factor". In the DFB diode lasers commonly used in spectroscopic gas sensors a can be in the range of from 2 to 5. One can also consider the effect of this phase noise as a random walk of the laser frequency within its Lorentzian line shape with a characteristic time $\tau_{Ph}$.

The semiconductor DFB diode lasers which are the most common laser sources in high sensitivity gas analysis are available from many vendors. Their linewidth according to vendors' specifications may vary from hundreds of kHz to about 10 MHz, which is close to the $\delta v_{Cav}$ values in typical high-finesse cavities. A 10 cm long buildup cavity with 99% mirror reflectivity has a resonance width $\delta v_{Cav}$=4.8 MHz (well within the range of the available DFB lasers linewidth values). On the other hand, the same cavity with available 99.999% reflectivity mirrors will have a linewidth of 4.8 kHz which is orders of magnitude narrower than the linewidth of available DFB lasers. The injection efficiency of the laser power will drop dramatically when the laser linewidth to the cavity resonance width ratio κ=$\delta v_{Las}$/$\delta v_{Cav}$ is larger than one. It is known that even for a slow passage of the laser line across the cavity resonance $\xi_{WM}$<<1 the average injection efficiency will decrease approximately as 1/κ, thus rendering useless further increase in the minors reflectivity as a means to increase the effective laser power acting on the PAS cell. Additionally, the smooth power buildup time profiles shown in FIGS. 2a-2b and in FIGS. 7a-7b can no longer be obtained. One would rather expect noisy bursts instead of these smooth profiles. This noise is a direct consequence of the lasers fundamental property i.e., phase noise, and cannot be eliminated by a feedback loop due to its random nature.

This is the situation typical for cavity ring-down spectroscopy with fast passage through resonance $\xi_{WM}$>>1 and a laser line width much broader than the cavity resonance width (κ>>1). The operating mode of the cavity-laser system in the present invention is different, and it requires additional analysis, as given below. As has been explained the passage should be slow ($\delta_{WM}$<0.15). In addition to that, we seek to keep increasing the cavity mirrors reflectivity to the maximum possible extent to maximize the intensity buildup, but not to impede the operation of the cavity peak to laser lock.

Figure 8:
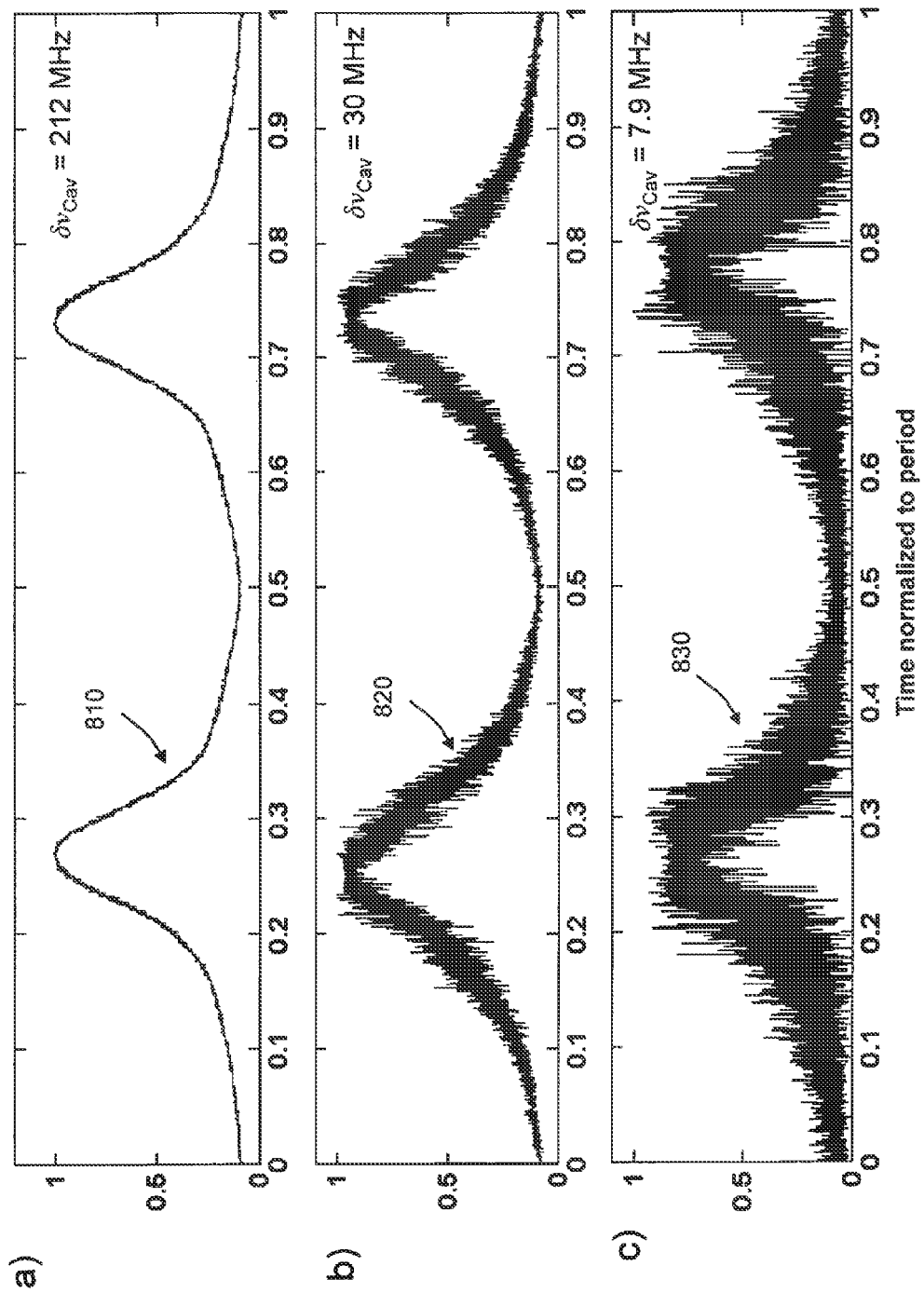
FIG. 8 shows experimental data for sweeping a laser with the specified line width of 2 MHz across the cavity resonances of different widths

In order to illustrate the determination of the limiting conditions for the limiting power buildup factor which is equivalent to the limiting reflectivity of the cavity mirrors one should refer to FIG. 8. A semiconductor DFB laser (NLK1C5JAAA manufactured by NEL), with its linewidth specified by the manufacturer to be 2 MHz, has been coupled into three different cavities, and the laser operating wavelength was periodically swept by application of the saw-tooth waveform across the resonance peak of each cavity. The modulation index was set to the optimum value for this waveform $m_w=2.79$. All three cavities have been made using two identical spherical mirrors having a reflection coefficient $R=1-4.4\times10^{-3}$ but having different cavity lengths of 1 mm, 7 mm and 21 mm. The finesse corresponding to this reflection coefficient was equal to 706, and therefore the cavities had different resonance widths $\delta v_{Cav}$, of 212 Mhz, 30 Mhz and 7.9 Mhz respectively. Traces a, b and c of FIG. 8 show the first photo-diode signals (which is proportional to the intracavity circulating power) for each cavity.

For the shortest cavity buildup trace 810 shown in FIG. 8a the DFB laser closely resembles the idealized trace 520 in FIG. 5 calculated for the same wavelength modulation conditions. The laser linewidth is about 100 times smaller than the cavity resonance width of 212 MHz, and as expected no substantial phase noise is visible on the trace. On the trace 820 in FIG. 8b for the 7 mm long cavity that has a 30 MHz bandwidth the laser phase noise becomes quite pronounced. Finally, the noise becomes very strong for curve 830 in FIG. 8c with the 21 mm long 7.9 MHz bandwidth cavity. The locking of the cavity to the laser operates reliably in all three cases. Attempts to further increase the cavity length results in intermittent operation of the cavity to laser locking system. The laser linewidth to the cavity bandwidth relation thus represents the limiting case.

The analysis of the traces in FIGS. 8 a-c gives one a quantitative criterion for the maximum cavity bandwidth allowed for a given laser linewidth. Trace 820 in FIG. 8b permits evaluation of the laser bandwidth. To further develop the analysis we refer to FIG. 9. In this Figure a single peak of FIG. 8b is shown with dots 910 representing an actual digitized first photo-diode signal. Solid line 920 is a Lorentzian fit of the intracavity circulation power resonance peak, and curve 930 displays fit residuals. A skilled artisan will understand that cavity resonance peak 920 acts as a frequency discriminator for the laser optical frequency random deviations due to the phase noise while the laser is being swept across the resonance peak. The deviations of the laser frequency are converted by the cavity into intensity deviations from the fit curve. In the middle area 940 of curve 920 the intensity increment of 0.1 of the total intensity corresponds to a frequency deviation of 3.0 MHz. In order for the cavity to serve as a frequency discriminator one needs the cavity decay time $\tau_{Cav}$ to be shorter than the phase correlation time $\tau_{Ph}$ of the laser which is indeed the case. For the 7 mm long cavity $\tau_{Cav}=5.3$ ns whereas $\tau_{Ph}=1/\pi\delta v_{Las}=159$ ns for the specified laser linewidth of 2 MHz. The peak to peak laser frequency deviation can now be determined from the part of the fit residuals 930 in FIG. 9 in the maximum slope area 940. The peak to peak intensity variation in curve 930 is 0.44 of the total intensity which means a peak to peak laser frequency excursion of 13.2 MHz or ±7.6 MHz from its average position. This peak to peak excursion is consistent with the laser linewidth of 2 MHz.

Figure 9:
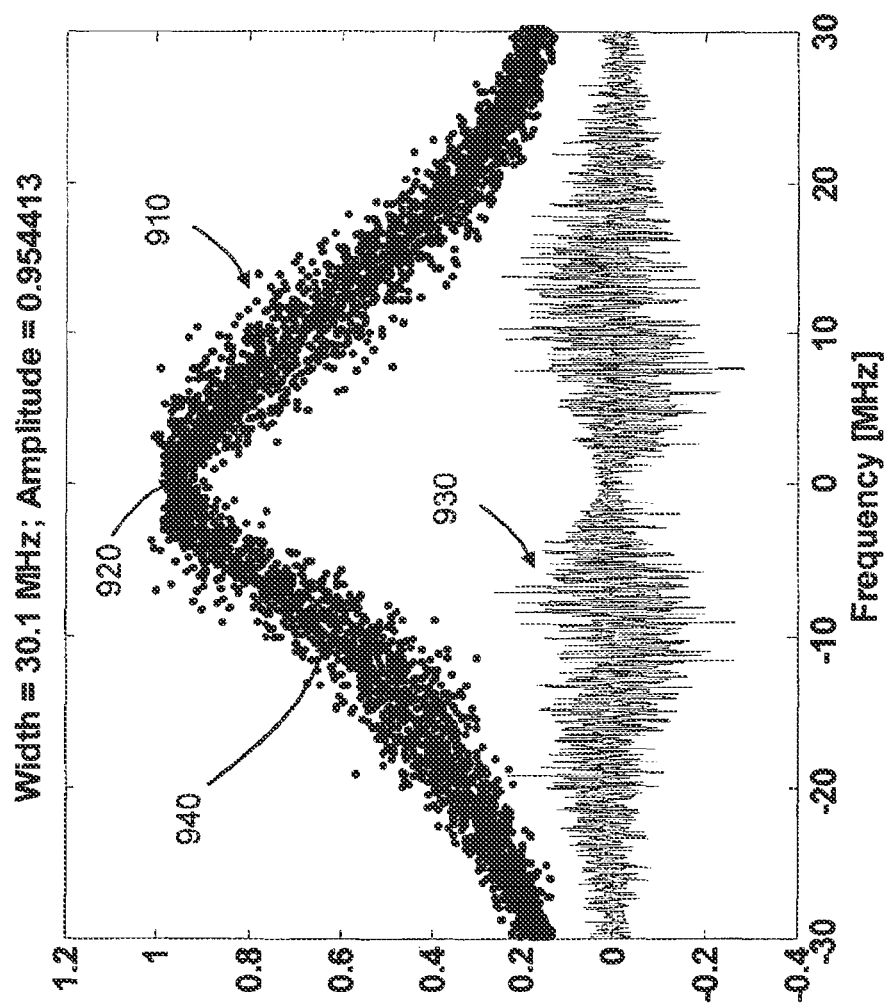
FIG. 9 illustrates the impact of the laser phase noise during the laser sweep across the resonance with a 30.1 MHz width

Now referring to FIG. 9 it can be seen that the total area of the intracavity circulating power peak can be determined from the amplitude of the fitted Lorentzian and is about 95% of the close to ideal peak in FIG. 8A. This signifies a reduced injection efficiency due to the laser phase noise.

Now looking at noisy trace 830 in FIG. 8c for the cavity with a 7.9 MHz bandwidth one sees a pronounced double-lobe appearance of the peaks. When, for example, the laser is at the middle of the cavity resonance curve slope, the 7.6 MHz excursion will bring the laser instantaneous frequency to the other side of the peak. The resonance peak area (injection efficiency) is further reduced and it is now about 84% of its ideal value with a narrow-linewidth laser.

Summarizing the analysis we have now shown that in accordance with the present invention, the mirrors reflectivities should be chosen such that the OPBC bandwidth $\delta v_{Cav}$, did not exceed three times the laser linewidth $\delta v_{Las}$, which is equivalent to the mathematical expression $\delta v_{Cav} \geq 3\delta v_{Las}$. This limitation sets a limit to the achievable power buildup once the PAS transducer has been chosen. As an example one can take a 6 cm long PAS cell as described by A. Rossi, et. al., (2005), Appl. Phys. Lett., 87, 041110 (2005) and the DFB laser from the example above. The buildup cavity should have minimum length of 8 cm to accommodate such a cell. The laser line width sets a limit to the cavity bandwidth of 6 MHz, which sets maximum value for the reflection coefficient for the mirrors to $R_1=R_2=0.99$. With a laser power coupled into the cavity of 10 mW, and the reduction of the injection efficiency due to the laser linewidth being 84% as described above, one can expect an intracavity buildup power of 1.68 W. Further assuming for the PAS the best NNEA reported so far of $1.2\times10^{-9}$ cm$^{-1}$W/$\sqrt{Hz}$, one can expect that such gas detector should be able to detect absorption coefficients as low as $7.1\times10^{-10}$ cm$^{-1}$ in a 1 Hz detection bandwidth. As it has been pointed out above, using cavity mirrors of unequal reflectivities, for the input mirror $R_1=0.98$, and for the cavity end mirror $R_2=0.99998$ so that the cavity bandwidth remains the same, we further increase the buildup power by an additional factor of two, to 3.36 W and consequently make the detection limit two times better, which will now become $3.6\times10^{-10}$ cm$^{-1}$/$\sqrt{Hz}$. Such a cavity configuration with unequal reflectivity mirrors is a preferred embodiment. Such sensitivity is quite competitive, for only two of the most sensitive (but significantly more complex) field systems, CRDS and ICOS a sensitivity of about $3\times10^{-11}$ cm$^{-1}$ has been reported.

One can further improve the detection limit by using DFB lasers with a narrower bandwidth and/or higher power, but one should make sure that there is no effect of the higher output power with a proportionally larger linewidth. There also exists an option to use a laser with an intrinsically narrower linewidth, such as for example an external cavity diode laser (ECDL). Linewidth values below 50 kHz have been reported for commercially available ECDLs. Unfortunately, such lasers usually have a reduced reliability and prohibitive price for many field applications. It is apparent from the analysis above that a limitation for achieving higher optical power inside the cavity comes from the size of the PAS cell itself. Otherwise, a ten-fold reduction of the cavity length could bring the sensitivity of the OPBC/PAS gas analysis system to the best reported values of all other spectroscopic methods. Unfortunately, various loss mechanisms inside traditional resonant PAS cells make much smaller cells that the one described above generally commercially impractical, as discussed in A. Miklos, et. al., Rev. Sci. Intr., 72(4), 1937-1955 (2001).

With a miniature sensor in a quartz-enhanced photo-acoustic sensor (QEPAS) [see U.S. Pat. No. 7,245,380 (2002) and A. Kosterev, et. al., Optics Letters, 27(21), 1902-1904 (2002)] a quartz tuning fork (QTF) of the thickness of only a fraction of a millimeter can be inserted into a very short cavity and thus offers a significant additional advantage in sensitivity which is difficult to achieve with traditional PAS cells simply due to their larger length. One should not forget however that a QTF alone has the NNEA about 20 times lower than a classical resonant PAS cell, which makes the benefit of using a single QTF within even a very small cavity somewhat less.

A combination of a QTF and micro-resonator tubes brings the QFT sensitivity up the level of a traditional resonant PAS cell, but with the penalty of a larger length and reduced immunity to the ambient noise. The length of such cell remains smaller though than that of a traditional resonant PAS cell.

Figure 10:
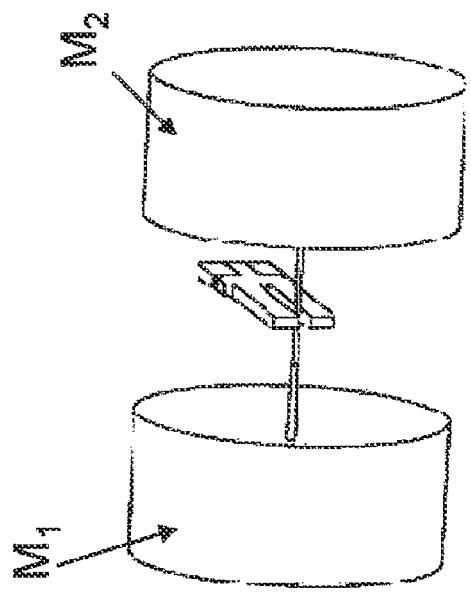
FIG. 10 shows a quartz tuning fork (QTF), and an example using a QTF inside an optical buildup cavity
Figure 10:
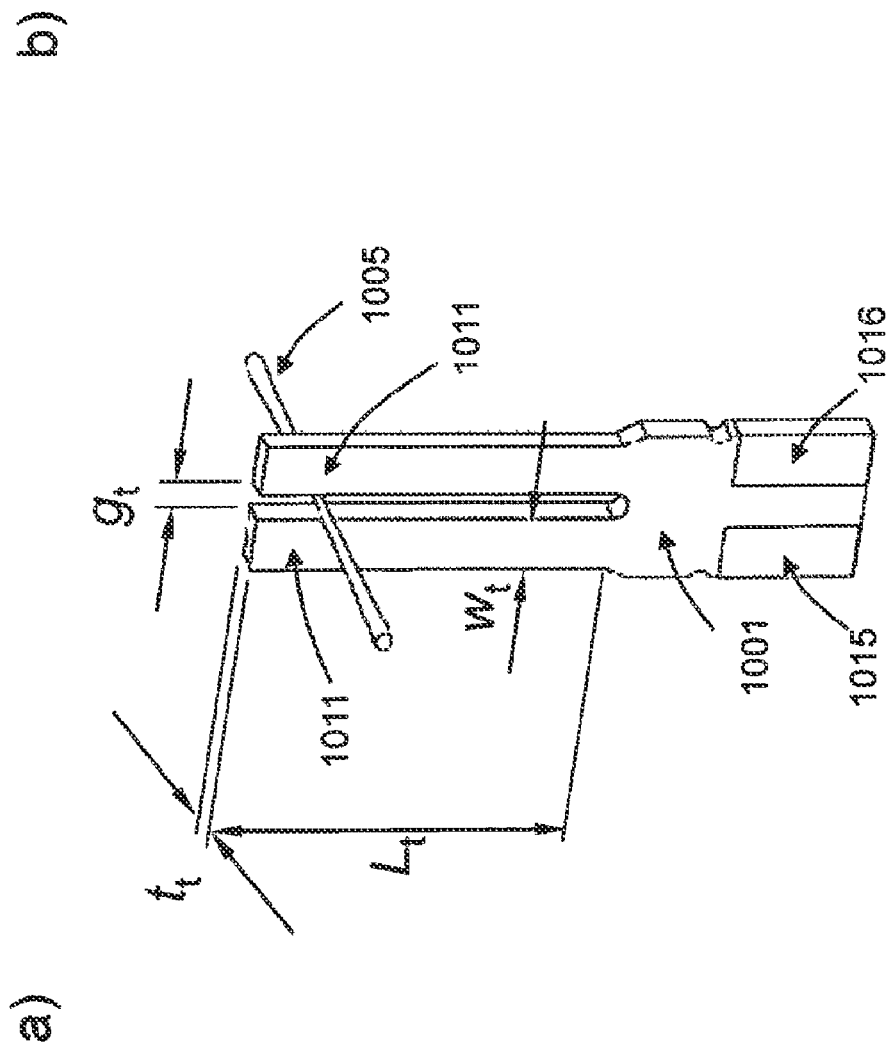

Several suitable configurations of OPBC with QTF will now be described following a brief summary of QTF features and properties. A slightly simplified drawing of an actual QTF 1001 with a fragment of optical beam 1005 is shown in FIG. 10A. The QTF operates as a transducer of the acoustic wave generated by optical beam 1005. We shall explain it on an example of a chopped (modulated in amplitude) laser beam, but a skilled artisan will easily make the extension of the explanation to the case of laser wavelength modulation. The chopped beam 1005 passes between the two tines 1011 and 1012 of the QTF. When the wavelength of the laser coincides with the absorption line of the analyte molecules of interest, then during the laser ON period the temperature within the beam area 1005 will be increasing, and during the laser OFF period it will be decreasing. The gas will tend to expand/shrink in the radial direction in a periodic manner, and this periodic expansion/contraction of the gas will excite a symmetrical vibration mode of the two tines 1011 and 1012 provided that the excitation matches the QTF resonance frequency. For a well balanced QTF there is no mechanical reaction from this symmetric mode motion into the fork base, and thus such motion possesses a very high Q-factor. In other words, the thermal excitation of the gas within the optical beam between the QTF tines will be significantly enhanced by the high-Q resonator of the QTF. On the other hand, the ambient acoustic waves coming to the QTF from a distant source in the form close to plane waves will tend to bend both tines in the same direction thus making the excitation of the useful symmetrical vibration mode inefficient. This explains the high QTF immunity to ambient acoustic noise. In contrast, even a very high sensitivity microphone is designed to acquire weak acoustic waves from a distant source, and it is not optimized for detecting perturbations emanating from a small-volume cylinder of air filled with a laser beam—exactly the opposite to what is needed for a high sensitivity analyzer of small impurities in gases. QTFs are made of crystal quartz as is evident from their name, and thus the vibrating QTF will generate an electrical current via the piezo-electric effect. For this purpose an electrode structure is deposited on the QTF. For simplicity in FIG. 10a only two contact pads 1015 and 1016 are shown. The electrode pattern on the QTF tines is not shown. The QTF dimensions may vary from manufacturer to manufacturer but the total length of a standard 32 kHz watch QTF does not exceed 8 mm, smaller than the wavelength which is about 10 mm. The particular QTF used in the examples below had a total length of 6.75 mm, its tine length $L_t$=4.0 mm, tine width $w_t$=0.62 mm, the tine thickness $t_t$=0.33 mm, and the gap between the tines $g_t$=0.29 mm. The QTF response to the photo-acoustical excitation depends upon the beam position inside the gap, it reaches its maximum at a beam distance close to the tine width from the tine end, and it rapidly decreases to both sides of the maximum, (see U.S. Pat. No. 7,245,380). The QTF performance as a photo-acoustic excitation transducer is a function of the QTF responsivity and of its noise. A detailed analysis of the QTF noise properties has shown that the QTF noise is determined by the thermal agitation of the surrounding gas molecules, and it thus represents the fundamental limit for acoustic wave detection. The best way to measure the QTF photo-acoustic response is to measure the current flowing between the pads 1015 and 1016, which is done with a standard transimpedance amplifier (TIA). The QTF oscillation and noise properties can be modeled using an electro-mechanical analogy with a series resistance, inductance, capacitance (RLC) circuit with the inductance L representing the fork tine effective mass, 1/C representing the force constant, and R representing the losses and the noise. These parameters can be determined by measuring the frequency dependence of the QTF response to electrical excitation. For this purpose one of the QTF contact pads should be connected to the sinusoidal electrical signal generator. The other pad remains connected to the TIA input. The amplitude and phase of the TIA output voltage permits one to determine all QTF equivalent circuit parameters L, C and R as well as a parasitic capacitance $C_p$ of the fork package and connecting wires. It is remarkable that not only can the fork resonance frequency $f_0$ and its quality factor Q be determined from these measured parameters as $$f_0 = \frac{1}{2\pi\sqrt{LC}}, \text{ and } Q = \frac{1}{R}\sqrt{\frac{L}{C}} \tag{7}$$

but also its noise current spectral density is also determined by its electric equivalent circuit parameters. The noise has a Lorentzian shape with the width equal to the QTF electrical response width, and its peak value is equal to the current noise density of its equivalent resistance:

$$I_{nQTF} = \sqrt{\frac{4k_BT}{R}} \tag{9}$$

This makes the QTF based PAS gas detector properties predictable, which is a great advantage in design; optimization and further development of QTF based gas sensors. The simplest configuration of OPBC/QEPAS which is a single QTF alone inside the cavity formed by two spherical mirrors $M_1$ and $M_2$ is shown in FIG. 10b. see, for example, A. Kosterev, et. al., Optics Letters, 27(21), 1902-1904 (2002). The QTF and the 7.75 mm diameter mirrors are drawn in a correct relative scale. The cavity length in this particular embodiment is 6.2 mm, but in other embodiments can be made as small as 1 mm, or even less, as long as the QTF fits between two cavity mirrors.

If one applies the limiting condition $\delta v_{Cav} \geq 3\delta v_{Las}$ to this case, one can find that with the same laser that has $\delta v_{Las}$=2 Mhz one can use the coupling minor with $R_1$=0.9984 and the second higher reflectivity mirror with $R_2$=0.99999 in order to get the minimum allowed cavity bandwidth of 6 MHz. As a worst case estimate, one can further assume that the loss of the coupling mirror is 10% of $(1-R_1)$. Under the same conditions as in the example above, with 10 mW of the laser power injected into the cavity one now can obtain about 22.2 W of the circulating power. This is under the condition that the power buildup coefficient for this cavity will be 2220. One can now make a sensitivity evaluation for this configuration. According to our measurements the QTF shown in FIG. 10a has a double-path responsivity to water vapor in ambient air of $R_{QTF}$=7.2 $\mu A/(cm^{-1}W)$, which means the QTF current resulting from photo-acoustic excitation of a medium that has an absorption coefficient of 1 $cm^{-1}$ with the laser power of 1 W double-passing the QTF is 7.2 $\mu A$. The QTF current noise can be found from the equivalent resistance of this QTF which at atmospheric pressure equal to 84.8 $k\Omega$ will be 0.437 $fA/\sqrt{Hz}$. Then the normalized noise-equivalent absorption (NNEA) for this QTF for water detection in the atmosphere can be found as follows: NNEA=$I_{nQTF}/R_{QTF}$=6.07×10$^{-8}$ cm$^1$W/Hz$^{1/2}$. Now if one takes into account our high intracavity power $P_c$, the noise equivalent absorption NEA can be found, NEA=NNEA/$P_c$=2.9×10$^{-9}$ cm$^{-1}$/√Hz.

An alternative embodiment reported in the literature (U.S. Pat. No. 7,245,380) corresponds to the highest QEPAS sensitivity so far without the OPBC. In this patent the NNEA for the H$_2$O molecule is at an optimum pressure of 60 Torr and with a double path through the QEPAS cell of 2.5×10$^{-9}$ cm$^{-1}$W/Hz$^{1/2}$. At close to atmospheric pressure (800 Torr) the NNEA degraded about two times to become 5.5×10$^{-9}$ cm$^{-1}$W/Hz$^{1/2}$, which is about 10 times better than that of QTF alone as previously reported. This sensitivity improvement should be credited to the use of a micro-resonator, see U.S. Pat. No. 7,245,380, A. Kosterev, et. al., Optics Letters, 27(21), 1902-1904 (2002) and A. Kosterev et. al, LACSEA 2006, Incline Village, Nev., February 5-9 (2006).

Figure 11:
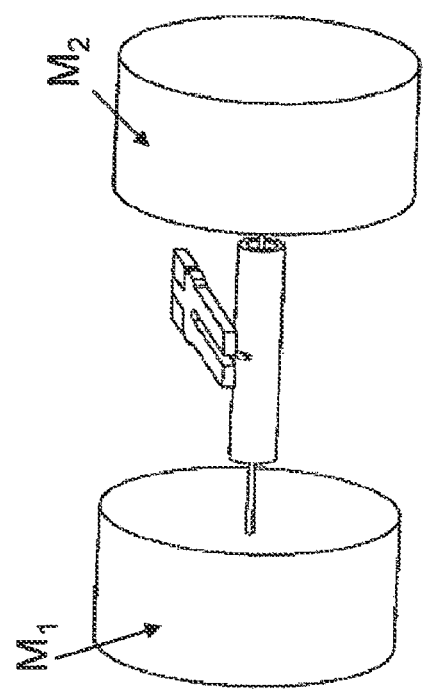
FIG. 11 shows a schematic view of two embodiments of the gas detection system of the present invention when a QTF with two kinds of micro-resonator tube system inside an OPBC
Figure 11:
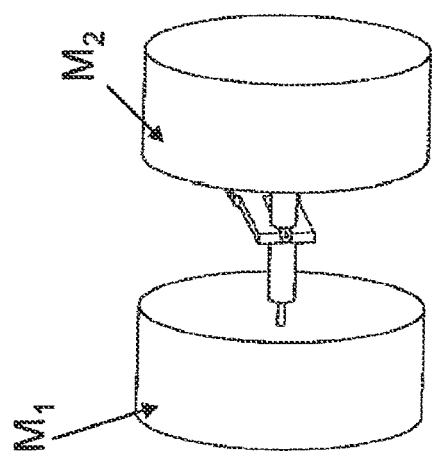

Two small tubes are positioned in close proximity to the QTF. The length of the tubes (~5 mm) was close to the acoustic half-wavelength in air. Utilizing the QTF with micro-resonator tubes is straightforward, with the only difference to the previous example being that now the cavity length should be long enough to accommodate the QTF and the tubes. A schematic of the QTF with the micro-resonator inside the OPBC is shown in FIG. 11a. It is similar to the configuration in FIG. 10b, except that now the cavity length is 12.4 mm such that there are gaps of about 1 mm between the micro-resonator tubes and the cavity mirrors. With the cavity length being two times larger than in the example in subsection 3.5.1 one needs to reduce mirror M$_1$ reflectivity twice in order to meet the requirement $\delta v_{Cav} \geq 3\delta v_{Las}$. If one leaves another mirror unchanged, then with M$_1$=0.9968 the cavity bandwidth remains 6.2 MHz>3$\delta v_{Las}$, the buildup factor is now 1200—two times lower naturally, and the circulating power in the cavity is 12.3 W. With the NNEA for this QTF-tubes combination, see A. Kosterev et. al, LACSEA 2006, Incline Village, Nev., February 5-9 (2006). one can evaluate the noise equivalent absorption to be 2.0×10$^{-10}$ cm$^{-1}$ Hz$^{1/2}$. The detection limit for water of this configuration can exceed the 90 ppbv demonstrated by A. Kosterev et. al, LACSEA 2006, Incline Village, Nev., February 5-9 (2006) to get an ~1000 fold improvement and thus become 0.09 ppbv. Even the simplest combination of the cavity and the QTF alone can provide a very impressive limit of detection of ~0.9 ppbv of water.

A skilled artisan would certainly appreciate that the above configurations have been given as examples, and that any current or future standard or without the cavity configuration of a QTF with signal enhancement tools can be used inside the OPBC by its insertion into the cavity and thus such configurations are within the scope of current invention. For example, single tube resonators can be used within the scope of the present invention inside the cavity. This configuration can be especially suitable for OPBC/QEPAS as discussed below. One author has suggested cutting a slit-like opening in the middle of a single small micro-resonator tube and positioning the QTF close to the opening. The optimization parameters for this combination besides the tube length are the tube inner and outer diameter, the slit depth and width, as well as the QTF position against the opening. The author evaluated experimentally several possible configurations and sizes and found by trial and error a few preferred ones. Their best reported result, achieved with an 8 mm long tube that had inner diameter of 0.45 mm and outer diameter of 0.70 mm, is 15.2 times enhancement of the responsivity for water in the atmosphere at normal temperature and pressure as compared with a single QTF.

We have found, however, that a preferred choice for OPBC/QEPAS is a different configuration which gives a responsivity enhancement of 10 times, but its tube length is only 5.84 mm which makes it fit into a shorter cavity as described previously and thus permits one to take full advantage of the 2200 times intensity buildup. The evaluation noise equivalent absorption for this configuration with a 10 mW of injected laser power gives an NEA=1.0×10$^{-10}$ cm$^{-1}$Hz$^{1/2}$ with an anticipated limit of detection for water of 45 pptv.

This configuration is shown in FIG. 11b. Besides using shorter tubes it provides several other important advantages for OPBC/QEPAS:

Shorter cavity length and a large inner tube diameter reduces the tube overlap with the field mode of the intracavity intense radiation, and results in lower background signals that may occur because of absorption in the tube walls.

This advantage becomes increasingly important at longer wavelengths because the cavity TEM$_{00}$ mode size increases as the square root of the wavelength. For a confocal cavity with the mirror radii of 6.2 mm the TEM$_{00}$ mode waist diameter at 1/e$^2$ intensity level is 0.078 mm for a laser wavelength of 1550 nm, but it increases to 0.199 mm at the wavelength of 10 μm. A substantial clipping of such beam would occur on a typical QTF itself with a gap between the tines of 0.29 mm. The inner diameter of the tube in a preferred embodiment is ~0.8 mm so that the beam intensity would drop 1/e$^8$ times, and the outer diameter is 1.20 mm.

It has been noticed that the QTF may respond to scattered laser radiation such as diffuse scattering from the mirror surfaces in the cavity, which may become significant at very high levels of optical power in the OPBC. In this configuration the QTF is entirely out of the optical beam, and it is shielded from the scattered radiation by the tube, resulting in a lower level of unwanted background signals.

The responsivity enhancement in the two-tube microresonator configuration is a function of the gap between the tube front surface and the QTF. The optimum value of the gap can be a few tens of micrometers only. Alignment of the fork and tubes in a two-tube configuration is difficult and should preferably be done actively, by monitoring the magnitude of the PAS signals. A single tube with a slit-shaped cut has a significantly larger tolerance margin of about 100 μm, which is a great benefit for gas sensor mass-production.

This configuration is one preferred embodiment.

The previously described examples represent the novel adaptation to an enhancement cavity of known QTF configurations that have heretofore been used with free-space laser beams. We will now describe further improvements of the QTF—micro-resonator structure inside the OPBC, and the method of its optimization which are included within the scope of the present invention.

The performance of a single tube micro-resonator can be further improved by increasing the interaction area between the QTF and the oscillating gas flow in and out the opening of the tube. According to the present invention this can be accomplished by cutting a flat face 1201 in the wall of the tube 1202 so that the flat face 1201 is parallel to the bottom of the cut 1203 as shown in the top part of FIG. 12A. The position of the QTF 1204 with the tube inside the OPBC is shown in the bottom part of FIG. 12A. The second cavity mirror is not shown. The reduced gap between the QTF and the tube will prevent the escape of the gas and increase the photo-acoustic response of the QTF-tube combination.

Figure 12:
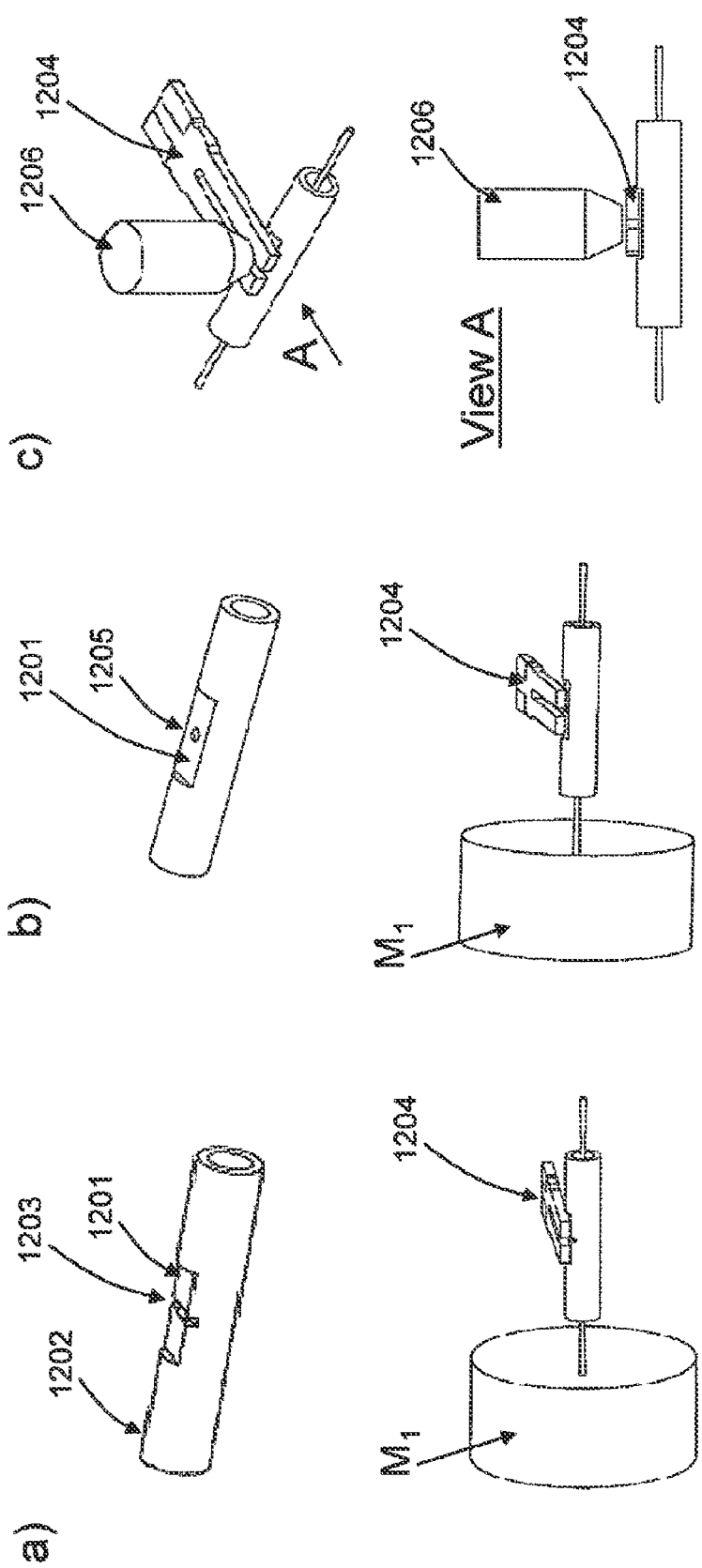
FIG. 12 presents schematic view of three versions of the improved single-tube microresonator of the present invention

The method of optimization of all design parameters of the QTF-microresonator combinations will now be described. A skilled artisan will appreciate that the shape of the opening in the microresonator tube need not necessarily be slit like. Other shapes, such as circular shape 1205 as shown in FIG. 12b, or oval shape, as well as chamfered openings can also be used for improving the efficiency of the oscillating gas delivery to the QTF tines. A flat face 1201 can also be used in combination with any shape of the opening.

In order to further prevent the escape of the oscillating gas, and transfer the oscillating motion of the gas inside the microresonator to the QTF tines with even higher efficiency, a pin 1206 with a flat end is suitably located close to the QTF such that the pin axis is within the opening area, and the pin flat end is parallel to the flat face 1201 and the QTF 1204 as shown in FIG. 12c.

As follows from Equation (9), the QTF sensor noise is determined by the inverse square root of the QTF resistance R. If one places the QTF into or near a micro-resonator, or simply place any object in a close enough proximity to the QTF, not only will the responsivity of the QTF to the photo-acoustic excitation ($R_{QTF}$) change, but as well its equivalent resistance and hence the noise $I_{nQTF}$ will change. This will directly influence the main gas detection system performance parameter—NNEA=$I_{nQTF}/R_{QTF}$. It has been observed experimentally that positioning the QTF between two micro-resonator tubes increases its equivalent resistance R and reduces its quality factor Q. If the distance between the QTF and the tubes is not unduly short, then the responsivity $R_{QTF}$ becomes larger than for an isolated QTF. At distances of about the thickness of the viscous boundary layer for the ambient gas the responsivity starts dropping. A possible reason for such a decrease is the tube slowing down the tines motion through viscous friction. Similar behavior is typical for any method that can be utilized to enhance the QTF response, with a single microresonator tube or two tubes. The conclusion is that the true QTF sensitivity optimization process alongside with measurement of the QTF responsivity should include an evaluation of the noise and maximizing the ratio $I_{nQTF}/R_{QTF}$. We have found this can be accomplished as follows:

- Measure QTF/micro-resonator system responsivity $R_{QTF}$ for a calibration gas at its standard conditions (concentration, temperature, pressure) by excitation with wavelength or amplitude modulated laser radiation that has a calibrated power for a certain value of the optimization parameter, for example the gap between the QTF and the microresonator tube.
- Measure the frequency dependence of the QTF/micro-resonator system amplitude response to electrical excitation as a function of the electrical excitation frequency.
- Determine the equivalent electrical circuit parameters for the QTF/micro-resonator system from the electrical response measured in the previous step
- Calculate the noise current density $I_{nQTT}$ using Equation (9) and the NNEA=$I_{nQTF}/R_{QTF}$.
- The best value of the parameter under optimization is the one giving the minimum NNEA.
- Now the process can suitably be re-iterated for another optimization parameter.

Figure 13:
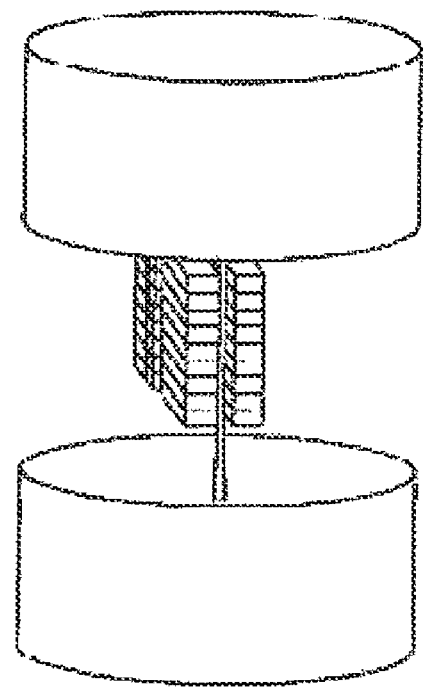
FIG. 13 shows a stack of 9 QTFs within an OPBC

The importance of this process can be illustrated by the fact that in the optimization process for a two-tubes/QTF system the highest gain in the responsivity alone was 18.6 times, whereas the gain in NNEA which is equivalent to the gain in sensitivity was 26.0 times as compared to a single QTF We now describe an alternative embodiment of the present invention for increasing the sensitivity of the QTF using combinations of multiple QTFs. We have observed that making a combination of two or more QTF, connecting them electrically in parallel such that the currents of individual QTFs add together in the TIA, and making the distance between the neighboring QTFs smaller than the thickness of the boundary layer for the gas surrounding the QTFS increases significantly the combination response as compared to a single QTF. We have further found that the responsivity of the combined QTF is increases nonlinearly with the number of the combined QTFs. The responsivity of two QTFs is 2.4 times higher than that of either of the two, the responsivity of four QTFs is 9.3 times higher, and for six QTFs the responsivity is 15.2 times higher—close to the maximum gain in responsivity obtained previously using combinations of a single QTF and micro-resonator tubes. The total thickness however, of the 6 QTF combination is only 2.2 mm whereas the total length of the best QTF and two tubes combination is about 10 mm. A cavity three to four times shorter can be used with the multiple forks combination thus permitting three to four times higher power buildup and correspondingly higher sensitivity. A schematic drawing of 9 QTFs inside a 6 mm long cavity is shown in FIG. 13.

The enhanced sensitivity of a QEPAS sensor can be obtained by combining two or more QTFs in the following way:

- Measure the acoustic response of several QTFs by sending a wavelength or amplitude modulated laser beam through the gap of each QTF and adjusting the laser wavelength to an absorption line of a calibration gas surrounding the QTF. Note the polarity of the QTF electrical signal, and mark the QTF contact pads corresponding to the same polarity as their electric response signals.
- position two or more QTFs together by aligning the tines and the gaps such that the light beam can pass through the combined gap in the same manner as with a single QTF.
- Ensure that the polarity marks are all on the same side of all the QTFs.
- In one embodiment—secure all the forks together by adhesive, or a mechanical fixture such that the gaps between adjacent forks are not larger than the thickness of the boundary layer.
- In an alternative embodiment one can adhere the bases of adjoining forks and also the opposing tips of adjoining fork tines together such as with an epoxy adhesive
- Connect all QTFs in parallel. With polarity marks aligned this will ensure that the signal currents of all QTFs will be additive. The forks combination is now ready to be used as PASA sensor having enhanced sensitivity A preferred embodiment of the invention for operation in the presence of optical feedback will now be described. An optical isolator 155 is used in a preferred embodiment of the invention as shown in FIG. 1 in order to significantly reduce the transmission of the light reflected from the cavity 160 back to the laser 101 in order to avoid the perturbations of the laser by this light. A large variety of compact and inexpensive optical isolators based upon Faraday Isolators is available for the visible, and especially for the near-Infrared ranges of the spectra. Usually, the longer the operating wavelength of the laser, the more difficult it is to achieve high performance optical isolation. This means that for detection of some species absorbing at longer wavelengths it may be not possible to avoid the retro-action of the light trapped inside the cavity on the laser. We will now describe the measures which not only permit one to keep high performance operation of the gas sensor in the presence of such retro-action or optical feedback, but actually improve this performance.

If optical feedback is present, even a small fraction of the radiation filtered by the optical transfer properties of the cavity and re-injected into the laser may substantially narrow down the laser emission spectrum provided that the phase of the re-injected radiation is correct. This makes it possible to have very high injection efficiency even with a laser that has its free-running line width much larger than the cavity resonance width. Additionally, the buildup factor in the presence of the optical feedback is no longer limited by the laser line width, and thus be made very high. The optical feedback therefore may be a positive phenomenon. However, if the phase of the re-injected radiation is wrong, the injection efficiency will be poor. The difficulty of maintaining the cavity in resonance and simultaneously keeping a correct phase may explains why no photo-acoustic system with an OPBC that utilizes optical feedback has been reported so far. With the present invention we can explain how to maintain the phase of the re-injected radiation on its correct value, and to build a gas detector that takes all advantage of the optical feedback.

In order to explain the principle of this invention we shall refer to optical feedback theory. Operation of diode lasers under the conditions of optical feedback has been studied both experimentally and theoretically in the late 1980s. A theoretical model that predicts the intensity inside the optical cavity, and the time dependence of the optical frequency of a diode laser as a function of the optical feedback phase and strength has been developed in an article by Ph. Laurent, A. Clairon. and Ch. Breant, IEEE J. Quantum Electronics, V. 25, No. 6. (1989), pp 1131-1142.

Figure 14:
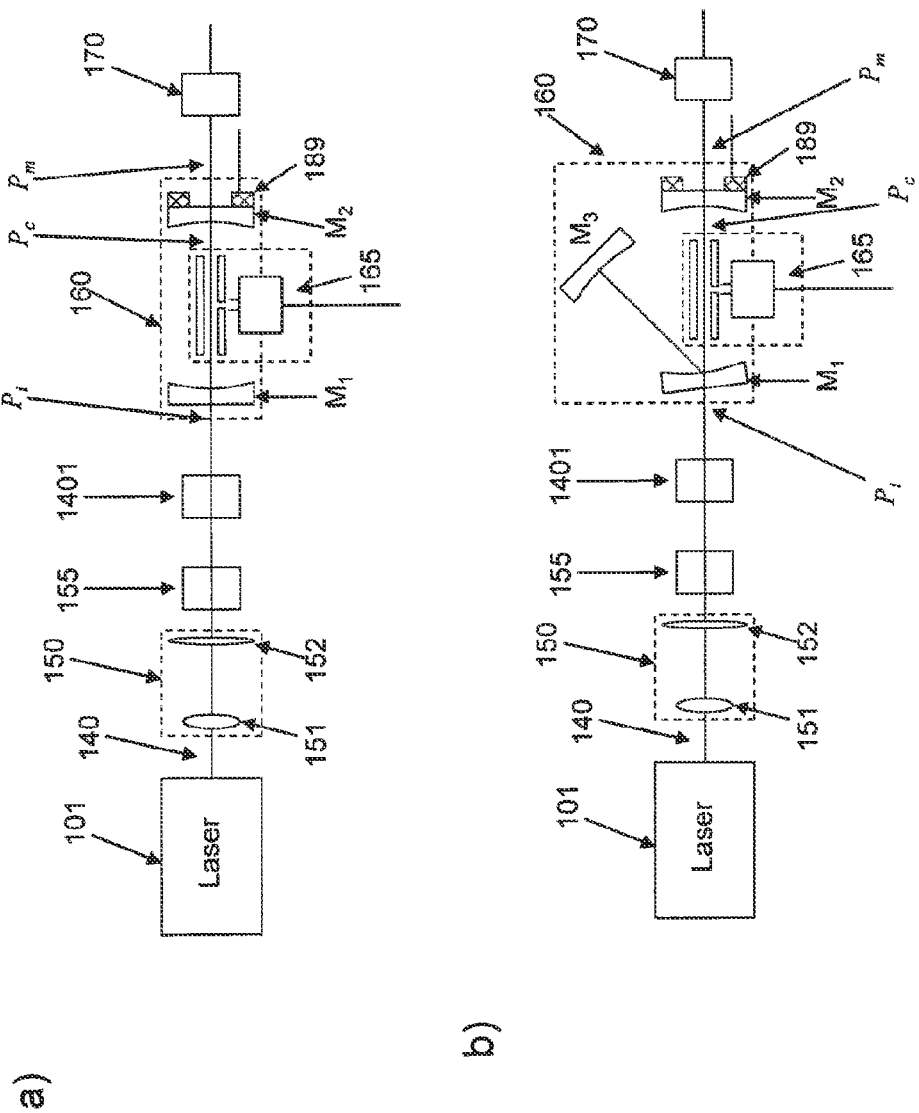
FIG. 14 shows two embodiments of the present invention with optical feedback where the optical isolator between the laser and the cavity is partially transmitting and thereby a portion of the light emerging from the cavity can re-enter the laser
Figure 15:
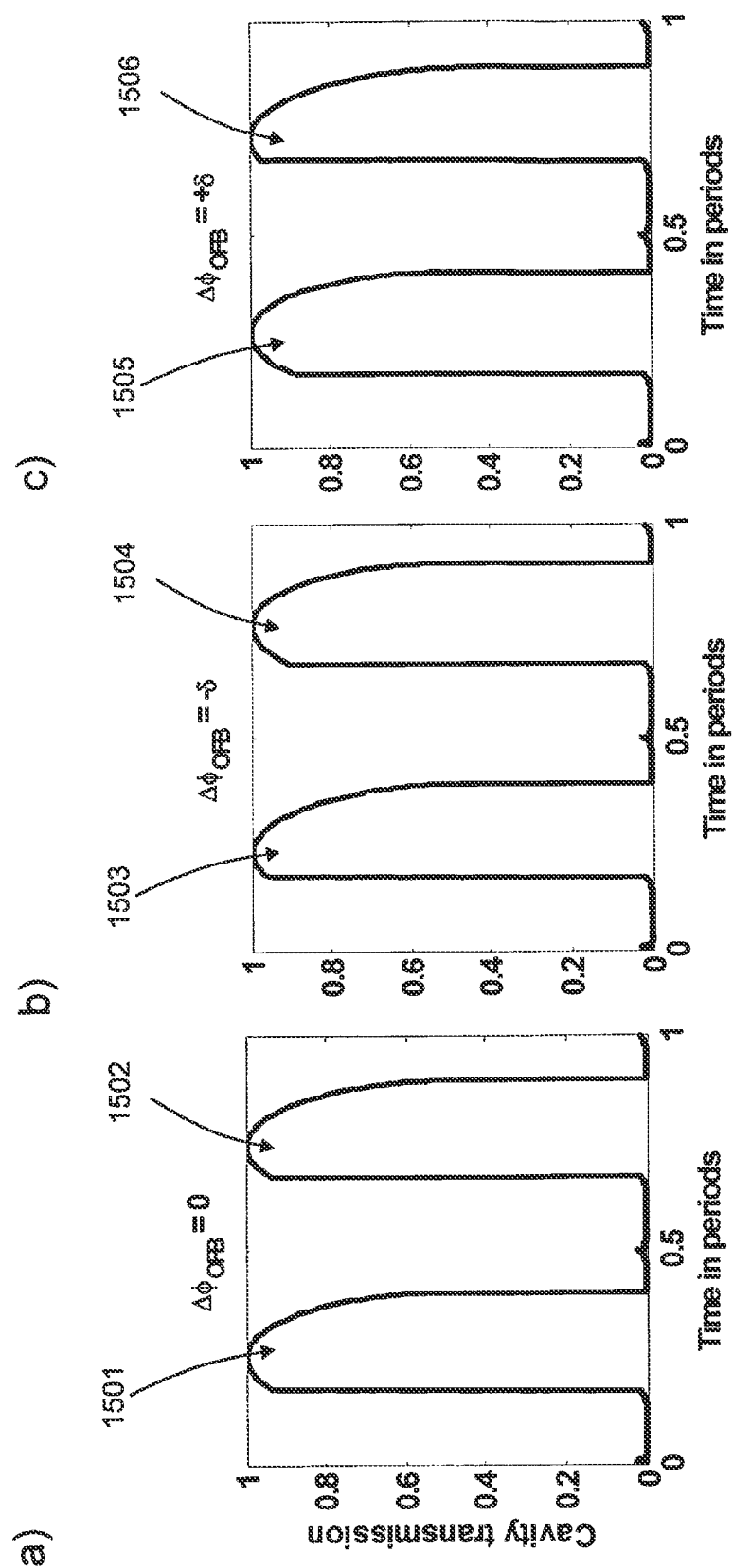
FIG. 15 shows examples of the waveforms on the output of the first photo-detector for three values of the optical feedback phase

The layout of the optical part of the gas detector in the presence of optical feedback is shown in FIG. 14A. An alternative implementation with a three-mirror cavity (V-cavity) is shown in FIG. 14b, but both layouts operate in a very similar way. The layout 14a is practically identical to the layout in FIG. 1 with the difference that an element 1401 capable to change the optical path difference between the laser 101 and the cavity input mirror $M_1$ has been added. Also, a part of the resonant optical radiation coming from the cavity 160 can now pass through optical isolator 155 to the laser 101. Changing the optical path will change the phase of the radiation that returns from the cavity 160 to the laser 101 through the cavity input mirror $M_1$. We therefore call the optical element 1401 a phasor. A skilled artisan would appreciate that such a phasor can be an electro-optical crystal with its index of refraction changing as a function of applied electric field, a mirror mounted on a piezo-electric transducer, or a slab of transparent material mounted on a thermo-electric cooler so that the optical path difference can be changed through the variation of the temperature dependent refractive index of the slab. The operation of the gas detector in the presence of the optical feedback is also nearly identical to its operation without feedback as it has been described above, except that now the magnitude and sign of the quadrature component of the time varying output signal of the first photo-detector 170 at the dither frequency designates the magnitude and the sign of the deviation of the optical feedback phase from its optimum value. In accordance with present invention, an additional module in the DPCU is periodically monitoring the magnitude and the phase of this signal and sending a value proportional to this signal to the input of the phasor 1401 so that the quadrature component zeroes out. This maintains a correct phase of the optical feedback at all times of the operation of the gas sensor. The principle of operation of the feedback phase lock can be easier understood from the diagrams in FIG. 15. All waveforms in this Figure correspond to the case when only $2 \times 10^{-4}$ fraction of the radiation emerging from the cavity re-enters the laser, nevertheless even such week feedback has a significant effect on the laser behavior and on the injection efficiency.

FIG. 15a shows optical intensity inside the cavity calculated using the model of Laurent et. al. for one up/down cycle of linear dither of the diode laser optical frequency for the case of ideal phase of the optical feedback $\Delta\phi_{OFB}=0$. One can see two peaks, peak 1501 occurs when unperturbed diode laser frequency ramps up, and peak 1502 when the unperturbed diode laser frequency ramps down. The shape of these peaks is significantly different from the peaks obtained without optical feedback and as shown in FIG. 2. They do not have a Lorentzian shape anymore because of the diode laser frequency pulling by the optical feedback. Besides, the unperturbed laser frequency peak to peak deviation in FIG. 2 is a very small fraction of the cavity FSR, whereas in this example it is close to one half of the cavity FSR. Again, this is due to the frequency pulling. However, the response to the laser and cavity detuning is the same as shown in FIGS. 2a and 2b. For zero laser and cavity frequency mismatch the two peaks 1501 and 1502 are situated symmetrically in the middle of the up- and down-ramp, as in FIG. 2A. When some cavity and laser detuning occurs, the peaks move towards each other, or from each other in exact analogy to FIG. 2b. This explains why the in-phase component of the time varying first photo-detector output signal at the dither frequency can be used to lock together the laser and the cavity, exactly as in the non-optical-feedback case. For zero optical feedback phase detuning two peaks 1501 and 1502 have the same shape and area, and thus the quadrature component of the time varying first photo-detector output signal at the dither frequency will be equal to zero. (to obtain the quadrature signal, peak 1501 is multiplied by the positive half-period of the cosine wave, and peak 1502 by the negative half period of this wave).

For small negative detuning $-\delta$ of the optical feedback phase $\phi$ the shape of the peaks is changing as shown in FIG. 15b. Now the peak on the up-ramp 1503 has a smaller area than the peak on the down-ramp 1504. The quadrature signal therefore will be negative indicating the direction and the magnitude of the optical feedback phase deviation or error signal for the phase locking. Similarly, for small positive detuning $+\delta$ of the optical feedback phase $\phi$ the shape of the peaks will become as it is shown in FIG. 15c. Now the area of the peak 1505 on the up-going ramp is larger than the area of the peak on the down-going ramp.

What is claimed is:

1. A method for the identification and quantification of one or more analyte species present in a gaseous or liquid medium utilizing a laser that outputs a laser beam and a resonant optical cavity containing said medium and having at least two cavity mirrors, one of which is a cavity coupling mirror, the method comprising:
   coupling the laser beam to the cavity via the cavity coupling mirror using mode matching optics;
   applying a periodic dither or modulation waveform to the optical frequency of the laser beam or to the laser itself to thereby induce modulation of the intracavity optical power;
   detecting, at the frequency of the applied dither or modulation waveform or harmonics thereof, a signal representing a varying pressure of the medium within the cavity;
   obtaining an electronic waveform signal proportional to the intracavity optical power by detecting an intensity of light emerging from a cavity mirror;

calculating a ratio of a magnitude of the varying pressure signal to a magnitude of the electronic waveform signal at the detection frequency; and simultaneously sampling the varying pressure signal and the electronic waveform signal for use in reducing noise in the varying pressure signal caused by noise in the optical signal of the incident laser beam.

2. The method of claim 1, wherein detecting is performed using a photo-acoustic transducer, and wherein the varying pressure signal is a photo-acoustic signal.

3. The method of claim 1, further including monitoring the intracavity light intensity, using a photodetector located external to the cavity, for use in locking a mean optical frequency of the laser to the frequency of the cavity transmission peak using first or other odd harmonics of the modulation waveform signal.

4. The method of claim 3, further including processing the varying pressure signal at the frequency of the modulation signal or harmonics thereof to produce a normalized pressure signal so as to compensate or correct for variations in the applied modulation waveform and/or variations in the intracavity optical power.

5. The method of claim 4, wherein detecting is performed using a photo-acoustic transducer, and wherein the varying pressure signal is a photo-acoustic signal.

6. The method of claim 1, further including obtaining an absorption spectrum of an analyte by scanning an optical frequency of the cavity resonance peak while maintaining a lock between a mean optical frequency of the laser and the cavity resonance peak.

7. The method of claim 6, wherein scanning the optical frequency of the cavity includes changing an optical length of the cavity.

8. The method of claim 7, wherein at least one of the cavity mirrors is moveable, and wherein changing the optical length of the cavity includes changing a physical length of the cavity by moving a movable cavity mirror.

9. The method of claim 8, further including maintaining a position of the movable cavity mirror within a displacement range, and if the mirror's position approaches a displacement range limit, resetting the mirror's position to a new position within the displacement range such that a new cavity resonance mode matches a mean optical frequency of the laser.

10. The method of claim 6, wherein maintaining the laser locked to the cavity includes obtaining an error signal and applying the error signal to control the laser mean optical frequency to thereby lock the mean optical frequency of the laser to the cavity resonance peak.

11. The method of claim 6, wherein maintaining the laser locked to the cavity includes obtaining an error signal and applying the error signal to control an optical length of the cavity to thereby lock the cavity resonance peak to the mean optical frequency of the laser.

12. The method of claim 1, further including:
obtaining an error signal; and
locking a cavity resonance peak to a mean optical frequency of the laser using the error signal.

13. The method of claim 1, wherein generation of the dither or modulation waveform is synchronous with sampling of the varying pressure and electronic waveform signals.

14. The method of claim 1, wherein a portion of the light emerging from the cavity coupling mirror reenters a cavity of the laser while maintaining an optical phase that results in periodic optical feedback locking whereby a mean optical frequency of the laser matches a resonance peak of the cavity.

15. The method of claim 1, further including optimizing the amplitude and shape of the applied periodic dither or modulation waveform.

16. A method for the identification and quantification of one or more analyte species present in a gaseous or liquid medium utilizing a laser that outputs a laser beam and a resonant optical cavity containing said medium and having at least two cavity mirrors, one of which is a cavity coupling mirror, the method comprising:

coupling the laser beam to the cavity via the cavity coupling mirror using mode matching optics;

applying a periodic dither or modulation waveform to the optical frequency of the laser beam or to the laser itself to thereby induce modulation of the intracavity optical power;

detecting, at the frequency of the applied dither or modulation waveform or harmonics thereof, a signal representing a varying pressure of the medium within the cavity, wherein a portion of the light emerging from the cavity coupling mirror reenters a cavity of the laser while maintaining an optical phase that results in periodic optical feedback locking whereby a mean optical frequency of the laser matches a resonance peak of the cavity, the method further comprising:

i) obtaining a time varying photo-detector output signal proportional to the intracavity optical power using a photo-detector located external to the cavity;

ii) obtaining a magnitude of an in-phase component of the time-varying photo-detector output signal at a dither frequency of the dither waveform;

iii) obtaining a magnitude of a quadrature component of the time-varying photo-detector output signal at the dither frequency;

iv) using the in-phase component to maintain a lock between the mean optical frequency of the laser and the resonance peak of the cavity; and v) increasing or decreasing an optical path difference between the laser and the cavity coupling mirror by inputting to an element adapted to vary the optical path difference between the laser and the cavity coupling mirror a value proportional to the magnitude of the quadrature component of the time varying photo-detector output signal at the dither frequency until the magnitude of the quadrature component zeroes down.

17. A method for the identification and quantification of one or more analyte species present in a gaseous or liquid medium utilizing a laser that outputs a laser beam and a resonant optical cavity containing said medium and having at least two cavity mirrors, one of which is a cavity coupling mirror, the method comprising:

coupling the laser beam to the cavity via the cavity coupling mirror using mode matching optics;

applying a periodic dither or modulation waveform to the optical frequency of the laser beam or to the laser itself to thereby induce modulation of the intracavity optical power;

detecting, at the frequency of the applied dither or modulation waveform or harmonics thereof, a signal representing a varying pressure of the medium within the cavity; and optimizing the amplitude and shape of the applied periodic dither or modulation waveform, wherein optimizing includes:

monitoring the intracavity optical power using a photodetector located external to the cavity; and repeatedly:
obtaining a magnitude of in-phase and quadrature components of an output signal of the photo-detector at the second harmonic of a dither frequency of the dither waveform;
determining a phase of second harmonic sine and cosine reference functions that zeroes out the quadrature component, and setting a constant phase relative to the phase of the dither waveform to this determined phase; and
determining an optimum laser wavelength dither amplitude that results in a maximum value of the in-phase component of the photo-detector signal at the second harmonic of the dither frequency.

18. The method of claim 17, wherein obtaining the magnitude of the in-phase and quadrature components of the photo-detector output signal includes multiplying the photo-detector output signal by a sine and a cosine reference function having the same frequency as the dither frequency and said constant phase relative to the phase of the dither waveform.

* * * * *